(12) United States Patent
Hahn et al.

(10) Patent No.: US 8,575,332 B2
(45) Date of Patent: Nov. 5, 2013

(54) CROSSLINKED POLYSACCHARIDE MICROPARTICLES AND METHOD FOR THEIR PREPARATION

(75) Inventors: Sei Kwang Hahn, Gotenba (JP); Tsuyoshi Shimoboji, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 685 days.

(21) Appl. No.: 10/579,032

(22) PCT Filed: Nov. 15, 2004

(86) PCT No.: PCT/JP2004/016948
§ 371 (c)(1),
(2), (4) Date: May 10, 2006

(87) PCT Pub. No.: WO2005/054301
PCT Pub. Date: Jun. 16, 2005

(65) Prior Publication Data
US 2007/0134334 A1   Jun. 14, 2007

(30) Foreign Application Priority Data

Nov. 14, 2003  (JP) ................................ 2003-385054
Dec. 5, 2003   (JP) ................................ 2003-407681
Sep. 7, 2004   (JP) ................................ 2004-259157

(51) Int. Cl.
   *C08B 37/00*   (2006.01)
   *A61K 9/50*    (2006.01)
   *A61K 9/62*    (2006.01)

(52) U.S. Cl.
   USPC ............................. 536/53; 536/55.3; 424/493

(58) Field of Classification Search
   USPC ................................. 536/53, 55.3; 424/493
   See application file for complete search history.

(56) References Cited

U.S. PATENT DOCUMENTS

| 587,913 | A |  | 8/1897 | Bates |  |
|---|---|---|---|---|---|
| 5,827,937 | A |  | 10/1998 | Agerup |  |
| 6,221,397 | B1 |  | 4/2001 | Russell-Jones et al. |  |
| 6,229,009 | B1 | * | 5/2001 | Lambert et al. | 536/123.1 |
| 6,620,927 | B2 | * | 9/2003 | Bulpitt et al. | 536/123.1 |
| 2001/0007665 | A1 |  | 7/2001 | Illum et al. |  |
| 2002/0177680 | A1 | * | 11/2002 | Hubbell et al. | 526/286 |
| 2002/0197328 | A1 |  | 12/2002 | Kim et al. |  |
| 2003/0012818 | A1 | * | 1/2003 | Schense et al. | 424/486 |
| 2003/0211166 | A1 | * | 11/2003 | Yamamoto et al. | 424/493 |

FOREIGN PATENT DOCUMENTS

| JP | 9-59303 A | 3/1997 |
|---|---|---|
| JP | 10-509696 A | 9/1998 |
| JP | 11-193246 A | 7/1999 |
| JP | 11-509256 A | 8/1999 |
| JP | 11-319066 A | 11/1999 |
| JP | 11-513047 A | 11/1999 |
| JP | 2000-5101000 A | 8/2000 |
| JP | 2000-248002 A | 9/2000 |
| JP | 2001-514316 A | 9/2001 |
| WO | WO 95/15168 A1 | 6/1995 |
| WO | WO 96/18647 A1 | 6/1996 |
| WO | WO 97/04012 A1 | 2/1997 |
| WO | WO 97/35562 A1 | 10/1997 |
| WO | WO 98/43664 A1 | 10/1998 |
| WO | WO 99/11703 A1 | 3/1999 |
| WO | WO 00/44808 A1 | 8/2000 |

OTHER PUBLICATIONS

Shu et al. Biomacromolecules, 2002, 3, p. 1304-1311.*
He, P., et al., "Chitosan microspheres prepared by spray drying", International Journal of Pharmaceutics, (1999), vol. 187, pp. 53-65.
Stahl, K., et al., "The effect of process variables on the degradation and physical properties of spray dried insulin intended for inhalation", International Journal of Pharmaceuticals, (2002), vol. 233, pp. 227-237.
Surendrakumar, K., et al., "Sustained release of insulin from sodium hyaluronate based dry powder formulations after pulmonary delivery to beagle dogs", Journal of Controlled Release, (2003), vol. 91, pp. 385-394.

* cited by examiner

*Primary Examiner* — Shaojia Anna Jiang
*Assistant Examiner* — Jonathan S Lau
(74) *Attorney, Agent, or Firm* — Browdy and Neimark, PLLC

(57) ABSTRACT

The present invention provides long-acting sustained-release formulations of drugs such as proteins or peptides, which are injectable, completely biodegradable and safe, as well as ensuring efficient encapsulation of the drugs such as proteins or peptides without inhibiting their biological activity. It is possible to achieve injectable sustained-release formulations that ensure efficient encapsulation and long-term sustained release of drugs such as proteins or peptides while retaining their biological activity, when a solution containing a drug and a polysaccharide derivative such as hyaluronic acid having a crosslinkable functional group(s) or a salt thereof is dehydrated in microparticulate form starting from a dilute state, where crosslinking proceeds slowly, to reach a concentration which facilitates crosslinking, to thereby cause crosslinking reaction during concentration, so that the drug is encapsulated into the crosslinked polysaccharide to give drug-carrying microparticles.

13 Claims, 13 Drawing Sheets

CROSSLINKED POLYSACCHARIDE MICROPARTICLES AND METHOD FOR THEIR PREPARATION

TECHNICAL FIELD

The present invention relates to sustained-release drug carriers composed of crosslinked polysaccharide microparticles which allow sustained release of drugs, more particularly pharmacologically active proteins or peptides, as well as a method for their preparation.

BACKGROUND ART

In recent years, an increasing number of formulations of pharmacologically active proteins or peptides have been developed for commercial use. However, such drugs usually have a short half-life in the blood and most of them are injections that must be administered repeatedly at frequent intervals, thus imposing excessive burdens on patients during drug administration. Hence, there is a demand for practical, sustained-release formulations of protein or peptide drugs, which exert their efficacy in as small amounts as possible and which permit reduced frequency of administration.

Sustained-release formulations of pharmacologically active proteins or peptides will cause denaturation or aggregation of the proteins or peptides during formulation preparation or sustained release, which results in a reduced recovery rate and constitutes a major obstacle to their development for commercial use. It has been attempted to prepare sustained-release formulations based on a biodegradable polymer matrix such as polylactic acid-polyglycolic acid copolymer (PLGA), but such formulations have been reported to cause protein denaturation and/or aggregation due to the hydrophobicity of the matrix, a drying step and/or a decrease in pH (see Non-patent Documents 1 and 2). On the other hand, there are also reports of sustained-release formulations based on a hydrophilic hydrogel matrix with reduced risks of these problems, but such formulations are not ready for commercial use. In terms of safety, a material used as a sustained-release matrix should combine non-antigenicity, non-mutagenicity, non-toxicity and biodegradability. Thus, no sustained-release formulation is now ready for commercial use in all aspects, i.e., encapsulation efficiency and recovery rate of proteins or peptides, as well as safety.

Some recent reports have proposed the use of polysaccharides as matrixes for drug carriers. Among them, hyaluronic acid (HA), a biomaterial (polysaccharide) isolated from the vitreous body of bovine eyes in 1934 by K. Meyer, has been known as a major component of extracellular matrix for a long time. HA is a kind of glycosaminoglycan composed of disaccharide units in which D-glucuronic acid and N-acetylglucosamine are linked to one another via $\beta(1\rightarrow 3)$glycosidic linkages.

There is no difference among species in the chemical and physical structure of HA and humans also have a metabolic system for HA; HA is therefore one of the safest medical biomaterials in terms of immunity and toxicity. Recent years have enabled microbial mass production of high-molecular-weight HA and also have allowed commercial use of HA in the fields of therapeutic agents for degenerated cartilage, cosmetics, etc.

There are also many reports of crosslinking techniques for HA as a matrix and sustained release formulations of protein or peptide drugs from HA gels. Techniques known for gelling HA via chemical crosslinking include the carbodiimide method (see Patent Document 1), the divinylsulfone method (see Patent Document 2), and the glycidyl ether method (see Patent Document 3). In general, when a protein or peptide is introduced into a crosslinked gel for encapsulation purposes, it results in a low introduction efficiency because of problems arising from compatibility and electrostatic repulsion between HA and the protein or peptide. In contrast, when in situ crosslinking is performed in the presence of a protein or peptide, it is advantageous in that the protein or peptide can be held in a gel at a high encapsulation efficiency. There are some reports showing that such in situ crosslinking is adapted for encapsulation of proteins or peptides into HA gels to give sustained-release formulations (see, e.g., Patent Document 4). However, there arises a problem of recovery rate when such an approach is used for in situ crosslinking of HA in the presence of proteins or peptides to prepare sustained-release formulations. As an example, a method is reported in which a HA derivative (HA-HZ) modified to have a hydrazide group (HZ) is crosslinked with a crosslinking agent comprising N-hydroxysuccinimide (NHS) (see Patent Document 5). This method is intended for in situ crosslinking under physiological conditions and limits crosslinkage formation at pH 7.4 to pH 8.5. However, the inventors' investigations have confirmed that this method also results in low recovery rates of proteins or peptides from the thus obtained HA gel. This is because the proteins or peptides will be partially reacted (mainly at their amino groups) with the crosslinking agent during crosslinking reaction to give crosslinked proteins. This method also suffers from a problem in that denatured proteins or peptides remaining in the gel have reduced biological activity and, if anything, are responsible for the cause of antigenicity. Although it is an essential requirement for pharmaceutical preparations that the encapsulated drug is released at a high recovery rate, no method is known for chemically crosslinking and gelling HA without causing proteins or peptides to react. Also, another method has been reported to encapsulate proteins or peptides at high recovery rates, in which polyethylene glycol (PEG) is used as a matrix and crosslinked through nucleophilic addition reaction of unsaturated functional groups (see Patent Document 6), but this method suffers from a problem in that fragments of non-biodegradable PEG remain unabsorbed.

In actual fact, to formulate such sustained-release materials into injectable formulations, these materials should be formulated in the form of microparticles. Spray dryers are widely used in such attempts and are also reported to be used in formulating insulin (see Non-patent Documents 3 and 4) and rh anti-IgE antibody (see Non-patent Document 5) in the form of microparticles, as well as in encapsulated drugs into hyaluronic acid microparticles (see Patent Documents 7 and 8). However, since the microparticles thus obtained will be dissolved in a short time in the subcutaneous tissues, they have a very short period of sustained release and are less practical for sustained release purposes. There is another report in which chitosan is crosslinked during spray drying so as to encapsulate low-molecular drugs therein (see Non-patent Document 6). However, the release period is as short as a few minutes in this case, and aldehyde used as a crosslinking agent is highly reactive with a functional group such as an amino group and hence cannot be used for proteins, peptides and other low-molecular drugs having a functional group(s) such as an amino group.

Patent Document 1: International Publication No. WO94/02517
Patent Document 2: JP 61-138601 A
Patent Document 3: JP 5-140201 A
Patent Document 4: U.S. Pat. No. 5,827,937

Patent Document 5: International Publication No. WO95/15168
Patent Document 6: International Publication No. WO00/44808
Patent Document 7: Japanese Patent No. 3445283
Patent Document 8: International Publication No. WO96/18647
Non-patent Document 1: J. Pharm. Sci., vol. 88, pp. 166-173, 1999
Non-patent Document 2: J. Microencapsulation, vol. 15, pp. 699-713, 1998
Non-patent Document 3: Int. J. Pharm. 233, 227-237, 2002
Non-patent Document 4: J. Control. Rel. 91, 385-394, 2003
Non-patent Document 5: Biotech. and Bioeng. 60, 301-309, 1998
Non-patent Document 6: Int. J. Pharm. 187, 53-65, 1999

DISCLOSURE OF THE INVENTION

Problems to be Solved by the Invention

As stated above, no method is known for preparation of injectable and biodegradable gel microparticles, which satisfies a high encapsulation efficiency, a high recovery rate and safety through in situ chemical crosslinking, drying, microparticle formation and drug encapsulation while retaining the biological activity of drugs such as proteins or peptides. Moreover, no example is known for long-acting sustained-release formulations of drugs such as proteins or peptides, which are prepared using such a method.

Means for Solving the Problems

As a result of extensive and intensive efforts made to overcome the problems stated above, the inventors of the present invention have found that drugs such as proteins or peptides can be efficiently encapsulated while retaining their biological activity when a solution of a drug and a hyaluronic acid derivative having a crosslinkable functional group(s) is concentrated starting from a dilute state, where crosslinking proceeds slowly, to reach a concentration which facilitates crosslinking, to thereby cause crosslinking reaction between HA molecules during concentration, so that the drug is encapsulated into the crosslinked hyaluronic acid. The inventors have also found that the crosslinked hyaluronic acid microparticles thus obtained are injectable and most suitable as biodegradable and safe microparticle carriers for long-term sustained release for the purpose of encapsulating drugs such as proteins or peptides. These findings led to the completion of the present invention.

Namely, the present invention relates to injectable sustained-release formulations of drugs such as proteins or peptides encapsulated in gels, which are obtained through in situ crosslinking, microparticle formation and drying while retaining the biological activity of the drugs such as proteins or peptides, as well as a method for their preparation.

Namely, in one aspect, the present invention provides a method for preparing crosslinked polysaccharide microparticles, which comprises the following steps:

a) preparing a dilute solution containing a polysaccharide derivative having a crosslinkable functional group(s);

b) dispersing the solution to form-microparticulate droplets; and c) concentrating the solution contained in the droplets to facilitate crosslinking reaction of the polysaccharide derivative. In another aspect, the present invention further provides such a method wherein step b) is a step in which the solution is dispersed by spraying to form microparticulate droplets.

In yet another aspect, the present invention also provides crosslinked polysaccharide microparticles which can be prepared by the above method.

The present invention will be further described in more detail below.

The polysaccharide derivative used in the present invention is not limited in any way as long as it is a polysaccharide derivative having a crosslinkable functional group(s). Among derivatives of glycosaminoglycans (acidic mucopolysaccharides including hyaluronic acid, chondroitin, chondroitin 4-sulfate, chondroitin 6-sulfate, dermatan sulfate, heparin, heparan sulfate, keratan sulfate, etc.), preferred are those having a crosslinkable functional group(s), and particularly preferred are hyaluronic acid derivatives having a crosslinkable functional group(s).

Thus, in yet another aspect, the present invention also provides a method for preparing crosslinked hyaluronic acid microparticles, which comprises the following steps:

a) preparing a dilute solution containing a hyaluronic acid derivative having a crosslinkable functional group(s);

b) dispersing the solution to form microparticulate droplets; and c) concentrating the solution contained in the droplets to facilitate crosslinking reaction of the hyaluronic acid derivative. In another aspect, the present invention further provides such a method wherein step b) is a step in which the solution is dispersed by spraying to form microparticulate droplets. In yet another aspect, the present invention also provides crosslinked hyaluronic acid microparticles which can be prepared by the above method.

The dilute solution found in step a) of the present invention is a solution containing substances such as a substrate and a reagent required for crosslinking reaction. However, the dilute solution is highly diluted with a solvent and hence the reaction does not proceed or proceeds very slowly in this solution. Although its concentration is not limited in any way, it is for example 0.1% to 5%, and particularly 0.2% to 3%. The solvent used in the present invention may be any solvent commonly used in the art or a mixture thereof and includes, without any limitation, water, DMSO, ethanol, N-methylpyrrolidone, and supercritical carbon dioxide fluid.

In step b) of the present invention, the dilute solution may be dispersed in the form of microparticulate droplets by using any technique commonly used in the art. Examples include, without any limitation, techniques for spraying the dilute solution and techniques to form an emulsion by mixing the dilute solution with another fluid. The microparticulate droplets thus obtained may have an average particle diameter of, for example, 0.04 µm to 1.5 mm, preferably 0.1 µm to 500 µm, without being particularly limited thereto.

In step c) of the present invention, the solution may be concentrated by any means as long as it allows the solution to be concentrated to reach a concentration at which the crosslinking reaction is further facilitated. This concentration step is also intended to include, e.g., a state where the solvent is completely removed such that the crosslinking reaction proceeds as a solid phase reaction.

Alternatively, the above steps b) and c) may be carried out in a single process. More specifically, the above steps b) and c) may be carried out in a single process by using techniques such as spray drying method, emulsion solvent evaporation method, and solvent diffusion method. Among them, spray drying is preferred for carrying out the above steps b) and c) in a single process.

The crosslinked polysaccharide microparticles of the present invention can be prepared when a solution containing a polysaccharide derivative having a crosslinkable functional group(s) is concentrated starting from a dilute state, where crosslinking proceeds slowly, to reach a concentration which facilitates crosslinking, to thereby crosslink the polysaccharide derivative during concentration. Likewise, the present invention is also characterized in providing drug-carrying microparticles that are obtained when a solution containing a drug and a polysaccharide derivative having a crosslinkable functional group(s) is concentrated starting from a dilute state, where crosslinking proceeds slowly, to reach a concentration which facilitates crosslinking, to thereby cause crosslinking reaction during concentration, in parallel with drying, so that the drug is encapsulated into the crosslinked polysaccharide.

The method provided by the present invention and the crosslinked polysaccharide microparticles (e.g., crosslinked hyaluronic acid microparticles) obtained by the method preferably have characteristics as shown below.

1. The method and microparticles ensure complete biodegradability and in vivo safety.
2. By grafting a polysaccharide such as HA with a crosslinkable functional group(s), the method and microparticles can keep a very short distance between crosslinking points (e.g., in the case of HA, about 3 nm when grafted at 33 mol % based on glucuronic acid) and are advantageous in achieving long-term sustained release.
3. The method and microparticles achieve a high crosslinking density.
4. When a protein is used as a drug, the method and microparticles can prevent protein denaturation.
5. Microparticle formation, drying and crosslinking can be carried out in a single process.

As used herein, the term "crosslinking" or "chemical crosslinking" is intended to mean containing intermolecular or intramolecular crosslinkages via covalent bonds. It may also mean having both intermolecular and intramolecular crosslinkages.

The crosslinking reaction used in the present invention is not limited in any way as long as it allows crosslinkage formation without causing drug denaturation even when crosslinkages are formed in the presence of drugs such as proteins or peptides. Examples of such a reaction include disulfide formation between mercapto groups, addition reaction between a mercapto group and an unsaturated bond, and reaction between a hydrazide group and an activated carboxylic acid ester.

The pH during crosslinking is not limited in any way, but it is preferably a pH at which crosslinkage formation is facilitated without causing protein or peptide denaturation so as to prevent reactions with amino groups contained in drugs such as proteins or peptides. Although such a pH can be selected as appropriate by those skilled in the art, it ranges from, for example, pH 3.0 to pH 9.0, and preferably pH 4.5 to pH 9.0.

The polysaccharide derivative used in the present invention is not limited in any way as long as it is crosslinkable as described above. Specific examples include hyaluronic acid derivatives (HA derivatives) having a crosslinkable functional group(s) introduced into HA. The crosslinkable functional groups used in the present invention include, without any limitation, a mercapto group, an unsaturated bond-containing group (e.g., a methacryl group, an acryl group, a vinylsulfone group, an acetylenecarbonyl group), and a hydrazide group (HZ group).

In a case where the crosslinking reaction is due to disulfide formation between mercapto groups, for example, crosslinkages can be formed using a polysaccharide derivative such as a HA derivative having mercapto groups, either alone or in combination with a crosslinking agent such as a compound having two or more mercapto groups (e.g., dithiothreitol (DTT), butanedithiol, polyethylene glycol dithiol, a peptide having two or more cysteines). With the aim of achieving a higher reaction rate of crosslinking, compounds such as sodium tetrathionate (STT), dipyridyl disulfide and Ellman's reagent (DTNB) may be added. In this case, if unreacted mercapto groups remain in the resulting gel, they have a possibility of leading to protein or peptide denaturation. Thus, to maximize the reaction efficiency, these compounds may preferably be added in a 0.1- to 2-fold molar amount, more preferably in a 0.5- to 1.5-fold molar amount, relative to reactive mercapto groups.

Although there is no particular limitation on the method for preparing a polysaccharide derivative having mercapto groups, for example, HA may be converted into a tertiary ammonium salt form, dissolved in a polar organic solvent such as DMSO, and then reacted with a mercapto group-containing amine or hydrazide in the presence of a coupling agent. Examples of such a mercapto group-containing amine include, without any limitation, 2-aminoethane-1-thiol, 3-aminopropane-1-thiol, and thioglycolic acid hydrazide.

In the case of introducing mercapto groups into HA, it is also preferable to first introduce an amino group or a hydrazide group and then introduce a mercapto group into this amino or hydrazide group. For example, carboxylic acid in HA may be condensed with adipic acid dihydrazide (ADH) or a divalent compound containing HZ or amino groups (e.g., ethylenediamine, ethylenedioxybisethylamine) in the presence of a condensing agent to synthesize a hydrazide group-modified HA derivative (HA-HZ) or an amino group-modified HA derivative (HA-amino group), which may then be reacted with, e.g., N-succinimidyl 3-[2-pyridyldithio]propionate (SPDP) and treated with a reducing agent (e.g., DTT) to form mercapto groups, or alternatively, which may then be reacted with 2-iminothiolane (Trout's Reagent) at the hydrazide or amino groups.

Examples of a coupling agent include benzotriazol-1-yloxy-tris(dimethylamino)phosphonium hexafluorophosphate (BOP), benzotriazol-1-yloxy-trispyrrolidinophosphonium hexafluorophosphate (PyBOP), N,N'-carbonyldiimidazole (CDI), N,N'-dicyclohexylcarbodiimide (DCC), 1-ethyl-3-(3-dimethylaminopropyl)carbodiimide hydrochloride (EDC), EDC/3,4-dihydro-3-hydroxy-4-oxo-1,2,3-benzotriazine (HODhbt), N-ethoxycarbonyl-2-ethoxy-1,2-dihydroquinoline (EEDQ), 4-(4,6-dimethoxy-1,3,5-triazin-2-yl)-4-methylmorpholium chloride n-hydrate (DMT-MM), and 2-(1H-benzotriazol-1-yl)-1,1,3,3-tetramethyluronium tetrafluoroborate (TBTU).

The crosslinkable functional groups intended in the present invention may be introduced, for example, by converting carboxyl groups contained in polysaccharide molecules into mercapto group-, unsaturated bond-, amino group- or hydrazyl group-containing ester or substituted amido groups as shown below:

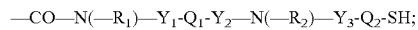
—CO—N(—R$_1$)—Y$_1$-Q$_1$-Y$_2$—N(—R$_2$)—Y$_3$-Q$_2$-SH;

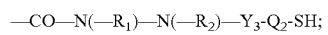
—CO—N(—R$_1$)—N(—R$_2$)—Y$_3$-Q$_2$-SH;

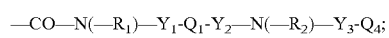
—CO—N(—R$_1$)—Y$_1$-Q$_1$-Y$_2$—N(—R$_2$)—Y$_3$-Q$_4$;

—CO—N(—R$_1$)—N(—R$_2$)—Y$_3$-Q$_4$; or

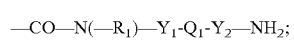
—CO—N(—R$_1$)—Y$_1$-Q$_1$-Y$_2$—NH$_2$;

(wherein $R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group, $Y_1$ represents a single bond, —N(—$R_3$)CO—, —N(—$R_3$)—, —CO— or —CH$_2$CO—, $Y_2$ represents a single bond, —CON(—$R_4$)— or —N(—$R_4$)—, $Q_1$ represents a linear or branched $C_{1-10}$ alkylene group, a linear or branched $C_{1-10}$ hydroxyalkylene group, a polyalkylene oxide group, a polypeptide group or a polyester group, $R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group, $Y_3$ represents a single bond, —CO—, —CO$_2$—, —CH$_2$—CH(OH)— or —CONH—, $Q_2$ represents a linear or branched $C_{1-10}$ alkylene group, a linear or branched $C_{1-10}$ hydroxyalkylene group, a polyalkylene oxide group, a polypeptide group or a polyester group, and $Q_4$ represents a linear or branched $C_{2-10}$ alkenyl group or a linear or branched $C_{2-10}$ alkynyl group).

Examples of a polysaccharide derivative having mercapto groups preferably include a hyaluronic acid derivative whose molecule contains at least one or more repeated structures represented by Formula (I):

[Formula 1]

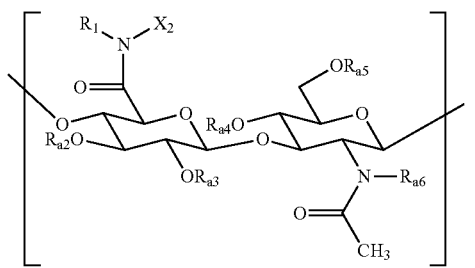

(I)

(wherein $X_2$ represents —$Y_1$-$Q_1$-$Y_2$—N(—$R_2$)—$Y_3$-$Q_2$-SH or —N(—$R_2$)—$Y_3$-$Q_2$-SH, $R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group, $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group or —SO$_2$OH, $Y_1$ represents a single bond, —N(—$R_3$)CO—, —N(—$R_3$)—, —CO— or —CH$_2$CO—, $Y_2$ represents a single bond, —CON(—$R_4$)— or —N(—$R_4$)—, $Q_1$ represents a linear or branched $C_{1-10}$ alkylene group, a linear or branched $C_{1-10}$ hydroxyalkylene group, a polyalkylene oxide group, a polypeptide group or a polyester group, $R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group, $Y_3$ represents a single bond, —CO—, —CO$_2$—, —CH$_2$—CH(OH)— or —CONH—, and $Q_2$ represents a linear or branched $C_{1-10}$ alkylene group, a linear or branched $C_{1-10}$ hydroxyalkylene group, a polyalkylene oxide group, a polypeptide group or a polyester group).

As used in Formula (I), the term "polyalkylene oxide group" refers to a group represented by —(CH(—R)CH$_2$O)$_n$—H (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

Moreover, in Formula (I), $R_1$ preferably represents a hydrogen atom, and $X_2$ preferably represents —$Y_1$-$Q_1$-$Y_2$—N(—$R_2$)—$Y_3$-$Q_2$-SH. In Formula (II), $Y_1$ preferably represents a single bond or —N(—$R_3$)—, $Y_2$ preferably represents a single bond, and $Q_1$ preferably represents a linear or branched $C_{1-4}$ alkylene group. In Formula (II), $R_2$ and $R_3$ each preferably represent a hydrogen atom, $Y_3$ preferably represents —CO—, and $Q_2$ preferably represents a linear or branched $C_{1-4}$ alkylene group.

In a case where addition reaction between a mercapto group and an unsaturated bond is utilized for crosslinking reaction, a polysaccharide derivative such as a HA derivative having unsaturated bond-containing groups may be mixed with a compound having two or more mercapto groups (e.g., dithiothreitol (DTT), butanedithiol, polyethylene glycol dithiol, a peptide having two or more cysteines, a mercapto group-modified HA derivative), or contrariwise, a polysaccharide derivative having mercapto groups may be mixed with a compound having two or more unsaturated bond-containing groups (e.g., ethylene glycol dimethacrylate, ethylenebisacrylamide, tris-2-maleimidoethylamine, 1,8-bis-maleimidotriethylene glycol, 1,4-bismaleimidyl-2,3-dihydroxybutane, a HA derivative having unsaturated bonds). In this case, it is preferable to add a basic compound such as triethanolamine for the purpose of improving the stability of proteins or peptides during crosslinking reaction and improving the reaction rate. The concentration preferred for this purpose is 10 μL/mL to 20 μL/mL. Examples of a compound having two or more mercapto groups also include a linear or branched $C_{2-10}$ alkylenedithiol (whose alkylene moiety may have one or more oxygen atoms inserted therein and/or may be substituted with one or more hydroxyl groups).

There is no particular limitation on the method for preparing a polysaccharide derivative having unsaturated groups, but it is difficult to achieve a high introduction rate, e.g., when glycidyl ether methacrylate or methacrylic anhydride is directly reacted with a hydroxyl group in HA (J. Biomed. Mat. Res. 54, 115-121, 2001). This is because HA will form a higher-order structure in an aqueous solution by the action of hydrogen bonding or hydrophobic interaction to reduce the reactivity of its functional groups including hydroxyl and carboxylic acid groups. A higher crosslinking density is desired to achieve prolonged sustained release of proteins or peptides. To this end, it is desirable to introduce a substituent at the carboxyl group of the glucuronic acid moiety. For example, HA may be converted into a tertiary ammonium salt form, dissolved in a polar organic solvent such as DMSO, and then reacted with an unsaturated bond-containing amine or hydrazide in the presence of a coupling agent such as 1-ethyl-3-(3-dimethylaminopropyl)carbodiimide (EDC), benzotriazol-1-yloxy-tris(dimethylamino)phosphonium hexafluorophosphate (BOP) or benzotriazol-1-yloxytrispyrrolidinophosphonium hexafluorophosphate (PyBOP) to prepare a desired derivative. Examples of such an unsaturated bond-containing amine include, without any limitation, allylamine, diallylamine, 4-amino-1-butene, acrylhydrazide, and methacrylhydrazide.

It is also preferable to introduce an amino group or a hydrazide group and then introduce an unsaturated bond-containing group into this amino or hydrazide group, as described above. For example, carboxylic acid in HA may be condensed with adipic acid dihydrazide (ADH) or a divalent compound containing HZ or amino groups (e.g., ethylenediamine, ethylenedioxybisethylamine) in the presence of a condensing agent (e.g., EDC, BOP, PyBOP) to synthesize a hydrazide group-modified HA derivative (HA-HZ) or an amino group-modified HA derivative (HA-amino group), which may then be reacted with an unsaturated bond-containing carboxylic acid derivative such as an acid anhydride or activated ester of $R_{10}$—COOH (wherein $R_{10}$ represents a linear or branched $C_{2-10}$ alkenyl group), preferably with methacrylic anhydride, N-hydroxysuccinimide (NHS)-activated acrylic acid, methacrylic acid or the like.

In a case where polysaccharide (e.g., HA) molecules are crosslinked via mercapto groups after introduction of unsaturated bond-containing groups, the ratio of mercapto groups to unsaturated bond-containing groups is not limited in any way and can be selected as appropriate by those skilled in the art. However, the ratio of mercapto groups to unsaturated bond-containing groups is preferably 3:1 to 1:2, more preferably 2:1 to 1:1, in order to minimize reactions with proteins or peptides, to prevent unsaturated groups from remaining in the gel and to ensure rapid reaction.

In a case where HA molecules are crosslinked via unsaturated bond-containing groups after introduction of mercapto groups, the ratio of unsaturated bond-containing groups to mercapto groups is not limited in any way and can be selected as appropriate by those skilled in the art. However, the ratio of unsaturated bond-containing groups to mercapto groups is preferably 3:1 to 1:2, more preferably 2:1 to 1:1, in order to minimize reactions with proteins or peptides, to prevent unsaturated groups from remaining in the gel and to ensure rapid reaction.

Examples of a polysaccharide derivative having unsaturated bond-containing groups preferably include a hyaluronic acid derivative whose molecule contains at least one or more repeated structures represented by Formula (II):

[Formula 2]

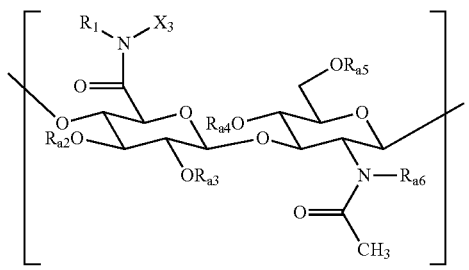

(II)

(wherein $X_3$ represents —$Y_1$-$Q_1$-$Y_2$—N(—$R_2$)—$Y_3$-$Q_4$ or —N(—$R_2$)—$Y_3$-$Q_4$, $R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group, $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group or —$SO_2OH$, $Y_1$ represents a single bond, —N(—$R_3$)CO—, —N(—$R_3$)—, —CO— or —$CH_2CO$—, $Y_2$ represents a single bond, —CON(—$R_4$)— or —N(—$R_4$)—, $Y_3$ represents a single bond, —CO— or —$CH_2CO$—, $Q_1$ represents a linear or branched $C_{1-10}$ alkylene group, a linear or branched $C_{1-10}$ hydroxyalkylene group, a polyalkylene oxide group, a polypeptide group or a polyester group, $R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group, and $Q_4$ represents a linear or branched $C_{2-10}$ alkenyl group or a linear or branched $C_{2-10}$ alkynyl group).

As used in Formula (II), the term "polyalkylene oxide group" refers to a group represented by —(CH(—R)$CH_2O)_n$—H (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

Moreover, in Formula (II), $R_1$ preferably represents a hydrogen atom, and $X_3$ preferably represents —$Y_1$-$Q_1$-$Y_2$—N(—$R_2$)—$Y_3$-$Q_4$. In Formula (II), $Y_1$ preferably represents a single bond, —N(—$R_3$)CO— or —N(—$R_3$)—, more preferably —N(—$R_3$)CO—. Likewise, $Y_2$ preferably represents a single bond or —CON(—$R_3$)—, more preferably —CON(—$R_3$)—, and $Y_3$ preferably represents a single bond, —CO— or —N(—$R_3$)—, more preferably —CO—. In Formula (II), $Q_1$ preferably represents a linear or branched $C_{1-4}$ alkylene group, $R_2$ and $R_3$ each preferably represent a hydrogen atom, and $Q_4$ preferably represents a linear or branched $C_{2-10}$ alkenyl group.

Likewise, examples of a polysaccharide derivative having mercapto groups include a hyaluronic acid derivative whose molecule contains at least one or more repeated structures represented by Formula (I) as mentioned above.

Reaction between a polysaccharide derivative such as a HA derivative having hydrazide groups and activated carboxylic acid may also be used for crosslinking reaction. Introduction of hydrazide groups into a polysaccharide may be accomplished in any manner known to those skilled in the art. For example, a carboxyl group in hyaluronic acid may be condensed with a divalent hydrazide-containing compound (i.e., a dihydrazide compound) in the presence of a condensing agent to synthesize a desired derivative. Examples of a dihydrazide compound include succinic acid dihydrazide, glutaric acid dihydrazide, adipic acid dihydrazide, and pimelic acid dihydrazide. Likewise, examples of a condensing agent include 1,3-dicyclohexylcarbodiimide, 1,3-diisopropylcarbodiimide, and 1-ethyl-3-(3-dimethylaminopropyl)carbodiimide. For example, carboxylic acid in hyaluronic acid may be condensed with adipic acid dihydrazide (ADH) in the presence of 1-ethyl-3-(3-dimethylaminopropyl)carbodiimide (EDC) to synthesize a hydrazide group-modified hyaluronic acid (HA-HZ). The crosslinking agent is not limited in any way as long as it has a functional group capable of reacting with a HZ group, and examples include molecules having, in the same molecule, two or more functional groups such as an NHS-activated ester group, a pentafluorophenoxycarbonyl group, a p-nitrophenoxycarbonyl group, an imidazolylcarbonyl group, an isothiocyanato group, a sulfonyl chloride group, a sulfonyl fluoride group, a formyl group, a vinylsulfonyl group, an acid anhydride and a 4-nitrophenylformate group. Illustrative examples of such a crosslinking agent include bis[sulfosuccinimidyl]suberate, disuccinimidyl glutarate, disuccinimidyl tartrate, and ethylene glycol bis[succinimidylsuccinate].

Taking into account the selective reactivity with a HZ group relative to an amino group, protein denaturation and the like, the pH during crosslinking is preferably pH 3.0 to pH 6.0, and more preferably pH 4.0 to pH 6.0. To maintain the pH within this range during crosslinking, the buffer to be used is preferably a less volatile one, as exemplified by citrate buffer. The crosslinking agent is used such that the amount of its functional groups capable of reacting with a hydrazide group is preferably 40 mol % or less, more preferably 20 mol % or less, particularly preferably 10 mol % or less, relative to hydrazide groups in a gel preparation solution.

Although there is no particular limitation on the rate of crosslinkable functional groups introduced into HA, it is preferably 5 mol % or more, particularly preferably 10 mol % or more, based on glucuronic acid in HA in order to obtain a non-flowable gel in vivo. Moreover, since the sustained release performance of a drug greatly depends on the crosslinking density of a crosslinked HA derivative, the sustained release period of the drug can be controlled by regulating this introduction rate.

Examples of a polysaccharide derivative having hydrazide groups include a hyaluronic acid derivative whose molecule contains at least one or more repeated structures represented by Formula (III):

[Formula 3]

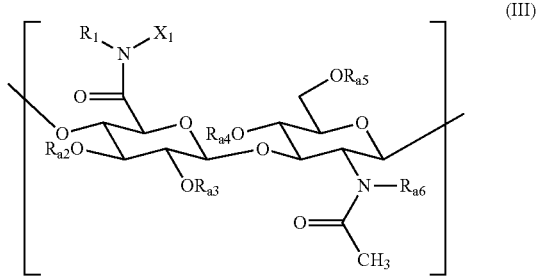

(III)

(wherein $R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group, $X_1$ represents —$Y_1$-$Q_1$-$Y_2$—$NHNH_2$, $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group or —$SO_2OH$, $Y_1$ represents a single bond, —$N(—R_3)CO$—, —$N(—R_3)$—, —$CO$— or —$CH_2CO$—, $Q_1$ represents a single bond, a linear or branched $C_{1-10}$ alkylene group, a linear or branched $C_{1-10}$ hydroxyalkylene group, a polyalkylene oxide group, a polypeptide group or a polyester group, $Y_2$ represents a single bond, —$N(—R_4)CO$—, —$CO$— or —$CH_2CO$—, and $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group).

Moreover, in Formula (III), $R_1$ preferably represents a hydrogen atom, $R_{a2}$, $R_{a3}$, $R_{a4}$, $R_{a5}$ and $R_{a6}$ each preferably represent a hydrogen atom, $Y_1$ preferably represents a single bond or —$CO$—, $Q_1$ preferably represents a linear or branched $C_{1-10}$ alkylene group, $Y_2$ preferably represents a single bond or —$CO$—, $R_3$ preferably represents a hydrogen atom, and $R_4$ preferably represents a hydrogen atom.

As used in Formula (III), the term "polyalkylene oxide group" refers to a group represented by —(CH(—R)CH$_2$O)$_n$—OH (wherein R represents a hydrogen atom or a linear or branched $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

The method of the present invention for preparing crosslinked hyaluronic acid microparticles may be any method in which crosslinking proceeds in parallel with drying of microparticles through solvent distillation. For example, by using a spray dryer for spraying and drying a fluid, a solution containing a drug and a hyaluronic acid derivative having a crosslinkable functional group(s) may be sprayed and dried so as to crosslink the hyaluronic acid derivative during concentration and drying, thereby obtaining drug-carrying microparticles in which the drug is encapsulated in the crosslinked hyaluronic acid. In the case of using the spray-dry technique, the drying temperature is preferably set at 100° C. or below in order to prevent drug denaturation.

Alternatively, a crosslinkable HA derivative (in a tetrabutylammonium salt form) and a drug may be dissolved in a polar organic solvent such as DMSO, followed by addition of a supercritical fluid such as carbon dioxide. DMSO may then be extracted to cause crosslinking reaction during concentration of hyaluronic acid, thereby obtaining microparticles. When using these techniques for microparticle formation, the addition of a surfactant such as Tween-20 or Tween-80 (around 1-2%) enables improvement in the recovery rate of the resulting microparticles. These techniques also require the use of a preparation solution which does not cause crosslinking reaction before concentration. The introduction rate of crosslinkable functional groups is preferably 5 mol % to 70 mol %, the molecular weight of hyaluronic acid is preferably 10,000 to 2,000,000 daltons, and the concentration of hyaluronic acid is preferably 0.1% to 5%, although they will vary depending on the time required for a process starting from mixing with a crosslinking agent until concentration, the introduction rate of crosslinkable functional groups, as well as on the molecular weight and concentration of hyaluronic acid.

In another method, an aqueous solution containing a drug and a hyaluronic acid derivative having a crosslinkable functional group(s) may also be emulsified in a dehydrating fluid (e.g., polyethylene glycol with a molecular weight of 400 daltons) to effect crosslinking of hyaluronic acid during dehydration/concentration, thereby obtaining drug-carrying microparticles in which the drug is encapsulated in the crosslinked hyaluronic acid. When using this method, a cationic or nonionic drug is preferred to improve the encapsulation efficiency.

Moreover, it is more preferable to perform thermal treatment after microparticle formation, so that the water content is further reduced and the crosslinking reaction is completely terminated. In this case, the crosslinking density is also improved and a prolonged sustained release can also be expected. The temperature required for thermal treatment is not limited in any way, but it may be performed, for example, at 30° C. to 110° C., preferably at 30° C. to 60° C.

Although the diameter of the dried microparticles may be optimized for their intended use, the diameter preferred for injectable purposes is usually 0.01 µm to 150 µm. For transnasal or transpulmonary administration, a diameter of 0.01 µm to 5 µm is preferred in terms of inhalation efficiency, while a diameter of around 0.01 µm to 0.2 µm is preferred for intravenous injection in terms of blood pharmacokinetics.

HA used in the present invention may be of any origin, including HA extracted from animal tissues, HA obtained by fermentation techniques, and HA chemically synthesized. Moreover, further treatment (e.g., hydrolysis) may be performed on HA. Modified HA prepared in various manners and its salts with alkali metals (e.g., sodium, potassium, lithium) also fall within the scope of HA according to the present invention. Although HA is often modified at its carboxyl or hydroxyl groups, the modified HA according to the present invention may be modified at any moiety. Such modified HA is not limited in any way and may receive any modification. Examples include sulfated HA (WO95/25751), N-sulfated HA (WO98/45335), esterified HA (EP0216453, WO98/08876, EP0341745), periodate-oxidized HA, and amide-modified HA.

There is no particular limitation on the molecular weight of HA used as a starting material in the present invention, and it is possible to use HA of any molecular weight. In general, HA of 5,000 to 3,500,000 daltons, preferably 10,000 to 1,000,000 daltons, can be used. The molecular weight and concentration of HA will affect the particle diameter of the resulting microparticles and hence may be selected as appropriate for the intended particle diameter.

Examples of a pharmacologically active protein or peptide include, without any limitation, erythropoietin (EPO), granulocyte colony-stimulating factor (G-CSF), interferons-α, β and γ (INF-α, β, γ), thrombopoietin (TPO), ciliary neurotrophic factor (CNTF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDFG), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathyroid hormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, and diabody. Moreover, the sustained-release drug carrier of the present invention can also be used for drugs of low-molecular-weight compounds. Examples of such low-molecular drugs include carcinostatic agents (e.g., alkylating agents, antimetabolites, alkaloids), immunosuppressive agents, anti-inflammatory agents (e.g., steroid drugs, non-steroidal anti-inflammatory agents), antirheumatic agents, and antibacterial agents (e.g., β-lactam antibiotics, aminoglycoside antibiotics, macrolide antibiotics, tetracycline antibiotics, novel quinolone antibiotics, sulfa drugs).

The sustained-release carrier of the present invention may be administered as a pharmaceutical composition in any dosage form suitable for the intended route of administration, in combination with one or more pharmaceutically acceptable diluents, wetting agents, emulsifiers, dispersants, auxiliaries, antiseptics, buffers, binders, stabilizers and the like. The route of administration may be either parenteral or oral.

EXAMPLES

Figure 1:
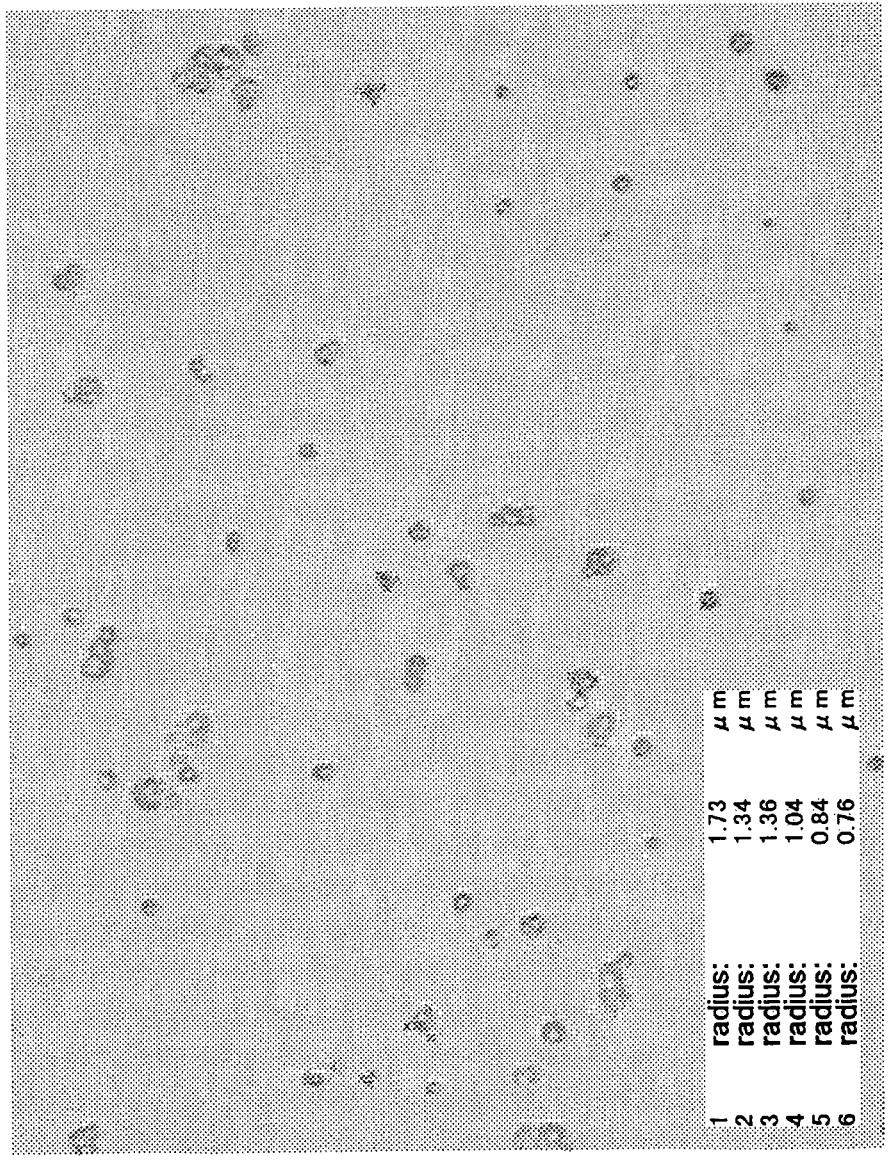
FIG. 1 One example of a microscopic photograph showing crosslinked HA-SH microhydrogel microparticles.

Preparation of EPO-Encapsulated Crosslinked Hyaluronic Acid Microparticles

The present invention will be further described in more detail in the following preferred examples, which are not intended to limit the scope of the invention.

NMR measurement was carried out using a nuclear magnetic resonance system JNM-ECA500 (JEOL. Ltd., Japan) and heavy water ($D_2O$) as a solvent. The introduction rate of each substituent was determined from the integral ratio between a peak unique to the introduced substituent and a peak derived from hyaluronic acid.

Example 1

Example 1-1

Synthesis of Hydrazide (HZ) Group-Modified Hyaluronic Acid Derivative (HA-HZ)

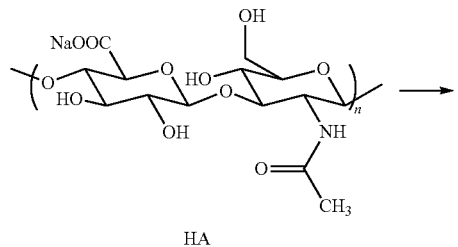

[Formula 4]

HA

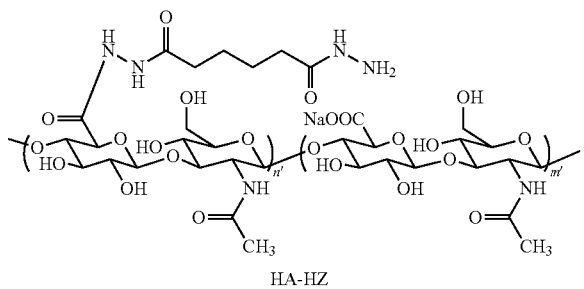

HA-HZ

Hyaluronic acid (HA) having a molecular weight of $1.9 \times 10^5$ daltons (200 mg, Denki Kagaku Kogyo Kabushiki Kaisha, Japan) was dissolved in distilled water at a concentration of 0.5% and adjusted with 5N hydrochloric acid to pH 4.7 to 4.8. 1-Ethyl-3-(3-dimethylaminopropyl)carbodiimide (EDC) and adipic acid dihydrazide (ADH) were added at a molar ratio of HA:EDC:ADH=1:0.3:40 (Batch 1-1), 1:1:40 (Batch 1-2) or 1:5:40 (Batch 1-3), and reacted while stirring at room temperature for 2 hours and adjusting the mixture with 5N hydrochloric acid to maintain a pH of 4.7 to 4.8. The reaction mixture was dialyzed against a 100 mM sodium chloride solution and a 25% ethanol solution (SpectraPor 7, molecular weight cutoff (MWCO): 12 k-14 k daltons) and lyophilized to give the titled HA-HZ.

The introduction rate of HZ groups in the resulting HA-HZ was determined for each batch by proton NMR, indicating that carboxylic acid in HA was modified with HZ at a rate of 26% (Batch 1-1), 46% (Batch 1-2) or 69% (Batch 1-3) (calculated by comparing N-acetyl groups in HA and HA-HZ (1.9 ppm, 3H) and methylene groups in the adipic acid-derived moiety of HA-HZ (1.6 ppm, 2.3 ppm, 2H each)).

Example 1-2

Synthesis of Mercapto (SH) Group-Modified Hyaluronic Acid Derivative (HA-SH)

[Formula 5]

HA-HZ ⟶

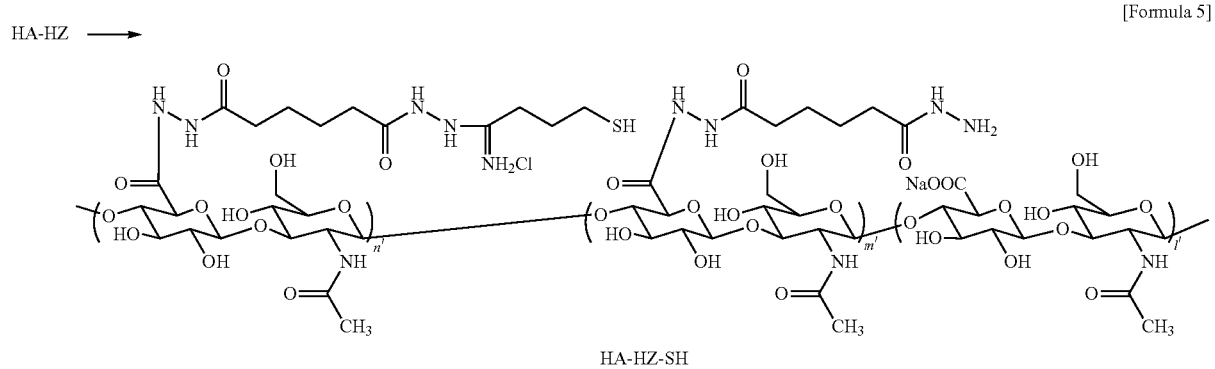

HA-HZ-SH

HA-HZ obtained in Batches 1 to 3 of Example 1-1 (100 mg each) was dissolved in 5 mL of 100 mM phosphate buffer, pH 8 (HA-HZ: 2% w/v), followed by addition of iminothiolane (ITL) (at a molar ratio of HZ/ITL=1/2). The mixture was reacted while stirring at room temperature for 2 to 4 hours and then precipitated in ethanol, washed three times and dried. The introduction rate of SH groups in the resulting HA-SH was determined for each batch by proton NMR and the results obtained are shown in Table 1 (calculated by comparing N-acetyl groups in HA and HA-SH (1.9 ppm, 3H) and methylene groups in the ITL-derived moiety of HA-SH (2.1 ppm and 2.7 ppm, 2H each)).

[Table 1]

TABLE 1

|  | Control | Batch 1 | Batch 2 | Batch 3 |
|---|---|---|---|---|
| HZ introduction | 0% | 26% | 46% | 69% |
| SH introduction | 0% | 20% | 35% | 56% |

Example 1-3

Preparation of EPO-Encapsulated Crosslinked Hyaluronic Acid Microparticles

HA-SH (introduction rate of SH groups: 20 mol %) obtained in Batch 1 of Example 1-2 (200 mg) and erythropoietin (EPO; 2 mg) were dissolved in 20 mL of 10 mM phosphate buffer (PB; pH 8) (stirring at room temperature for 1 hour), followed by addition of Tween-20 (4 mg) and sodium tetrathionate (STT; 22.3 mg, 1-fold molar amount relative to SH groups). This solution was spray-dried under the following conditions to obtain microparticles.
 Spray dryer: Buchi Mini spray dryer B-191
 Solution feed rate: 1.5 mL/min (Tygon tube, Pump speed 15%)
 Feed solution concentration: 10 mg/mL
 Atomizing air flow rate: 650 L/hr
 Drying air flow rate: 40 kL/hr (Aspiration speed=65%)
 Inlet temperature: 85° C. to 95° C.
 Outlet temperature: 50° C. to 60° C.

Example 2

The same procedure as shown in Example 1-3 was repeated to prepare EPO-encapsulated crosslinked hyaluronic acid microparticles, except that HA-SH (introduction rate of SH groups: 35 mol %) obtained in Batch 2 (200 mg) and sodium tetrathionate (STT; 39.0 mg, 1-fold molar amount relative to SH groups) were used in the experimental operation of Example 1-3.

Example 3

The same procedure as shown in Example 1-3 was repeated to prepare EPO-encapsulated crosslinked hyaluronic acid microparticles, except that HA-SH (introduction rate of SH groups: 56 mol %) obtained in Batch 3 (200 mg) and sodium tetrathionate (STT; 62.4 mg, 1-fold molar amount relative to SH groups) were used in the experimental operation of Example 1-3.

Example 4

The same procedure as shown in Example 1-3 was repeated to prepare EPO-encapsulated crosslinked hyaluronic acid microparticles, except that HA-SH (introduction rate of SH groups: 56 mol %) obtained in Batch 3 (200 mg) and sodium tetrathionate (STT; 38.9 mg, 0.7-fold molar amount relative to SH groups) were used in the experimental operation of Example 1-3.

Example 5

The same procedure as shown in Example 1-3 was repeated to prepare EPO-encapsulated crosslinked hyaluronic acid microparticles, except that HA-SH (introduction rate of SH groups: 56 mol %) obtained in Batch 3 (200 mg) and sodium tetrathionate (STT; 27.8 mg, 0.5-fold molar amount relative to SH groups) were used in the experimental operation of Example 1-3.

Example 6

The same procedure as shown in Example 3 was repeated to prepare EPO-encapsulated crosslinked hyaluronic acid microparticles, except that Tween-20 (4 mg) was replaced by Tween-80 (4 mg) in the experimental operation of Example 3.

Example 7

The same procedure as shown in Example 3 was repeated to prepare EPO-encapsulated crosslinked hyaluronic acid microparticles, except that Tween-20 was not added in the experimental operation of Example 3.

Example 8

The same procedure as shown in Example 3 was repeated to prepare EPO-encapsulated crosslinked hyaluronic acid microparticles, except that STT was not added in the experimental operation of Example 3.

Comparative Example 1

HA-SH (introduction rate of SH groups: 56 mol %) prepared in Batch 3 of Example 1-2 (33 mg) was dissolved in 690 μL of 10 mM phosphate buffer (pH 8.0), supplemented with 30 μL of an aqueous EPO solution (10 mg/mL) and stirred for 10 minutes, followed by addition of a solution prepared by dissolving sodium tetrathionate (STT; 9.3 mg, 1-fold molar amount relative to SH groups) in 30 μL of 10 mM phosphate buffer, pH 8.0. The resulting solution was filled in 250 μL volumes into 1 mL syringes and reacted at 37° C. for 5 hours to obtain cylindrical HA gels.

Comparative Example 2

The same procedure as shown in Example 8 was repeated to prepare EPO-encapsulated HA microparticles, except that HA-SH was replaced by HA in Example 8.

It should be noted that the microparticles obtained in Examples 1 to 8 and Comparative Example 2 were each collected at a rate of 50% to 65%.

Test Example 1

Measurement of Particle Diameter and Particle Water Content

Figure 2:
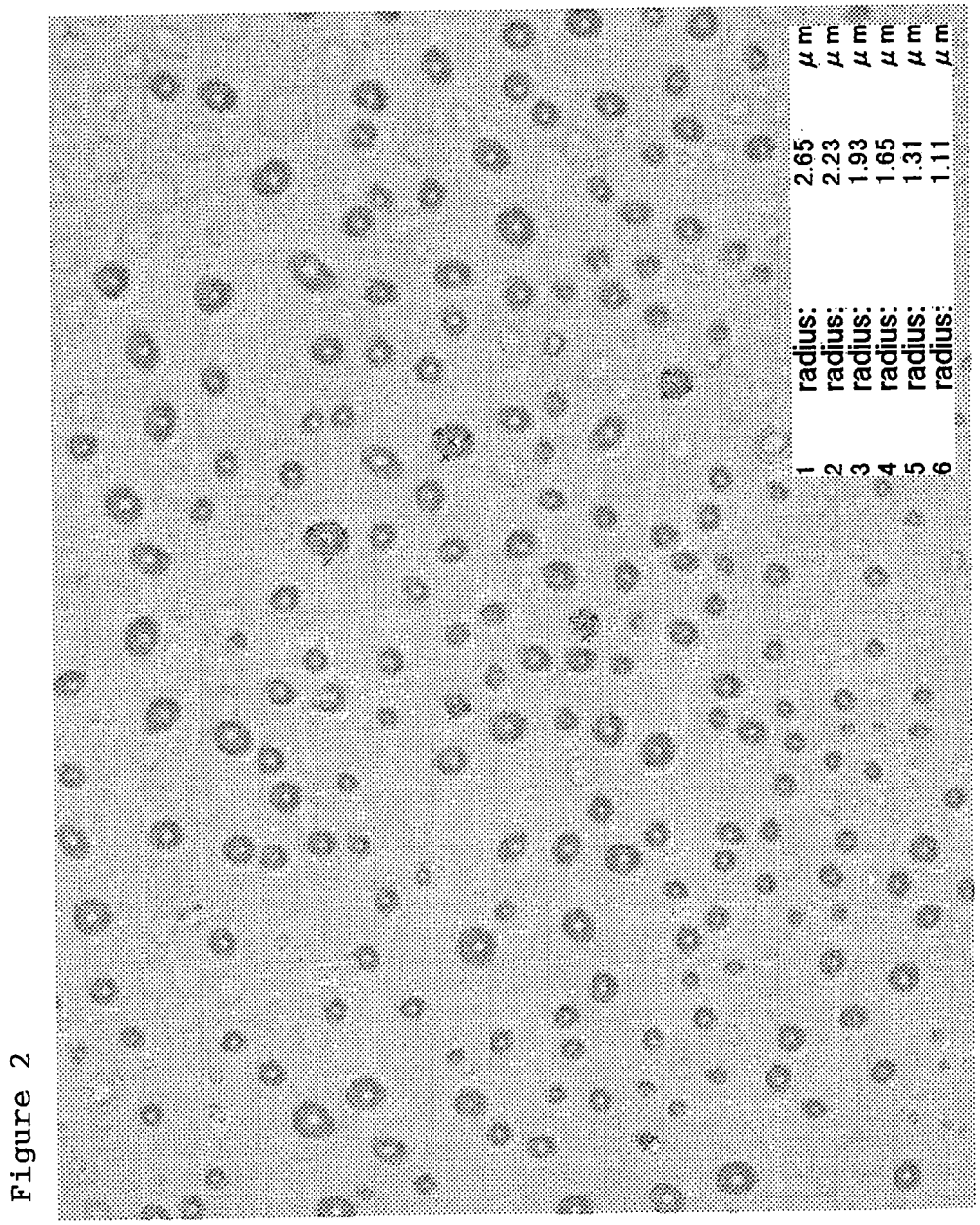
FIG. 2 One example of a microscopic photograph showing crosslinked HA-SH microhydrogel microparticles swollen in PBS.

FIG. 1 shows a microscopic photograph of the microparticles prepared in Example 3 (×3000 magnification). FIG. 2 shows a microscopic photograph of these microparticles when dispersed in PBS (×3000 magnification). The particle diameter of these microparticles was about 1.2 μm (dried) and about 1.8 μm (swollen with water).

Figure 3:
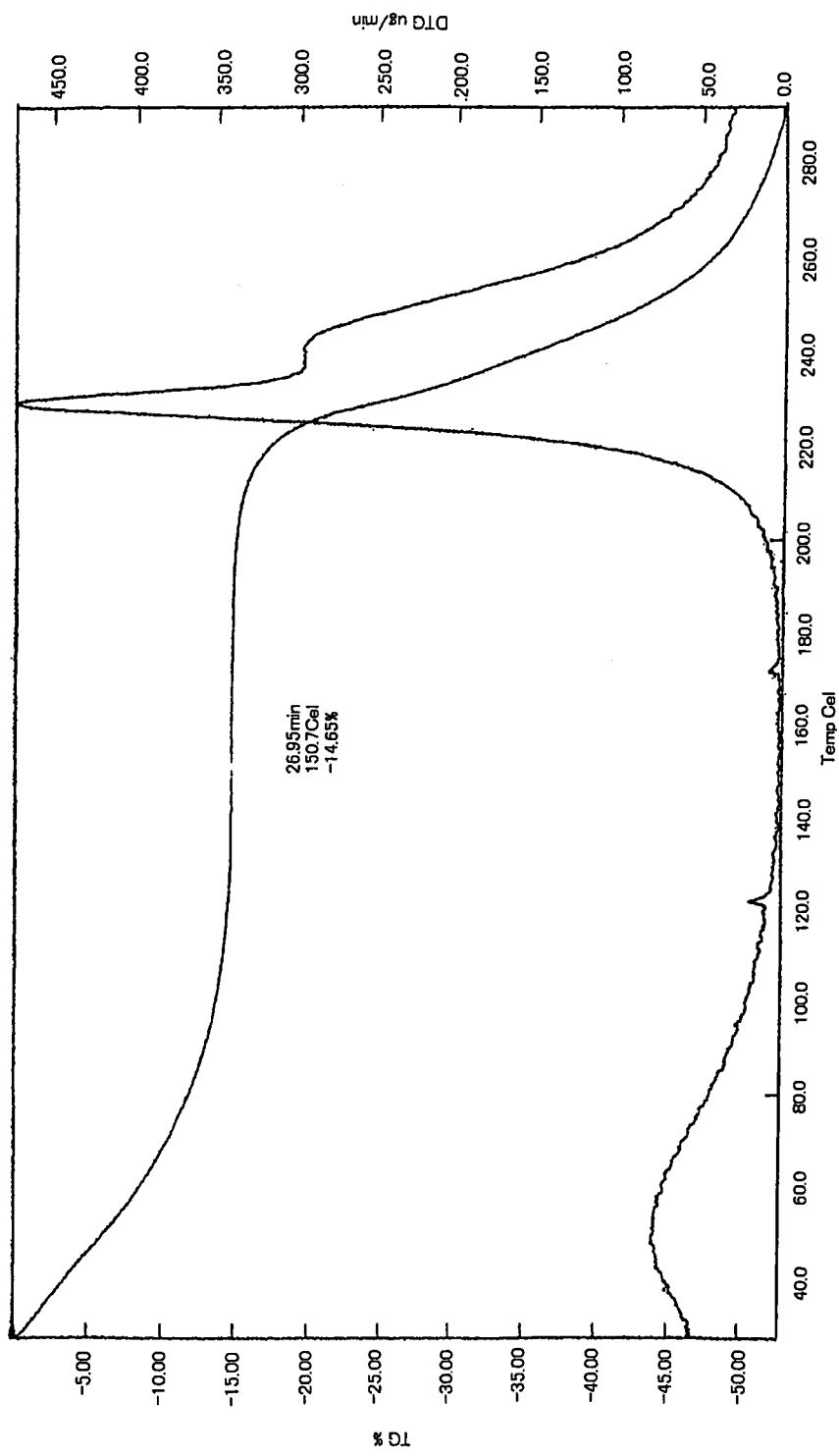
FIG. 3 One example of the thermogravimetric results analyzed for an EPO-encapsulated crosslinked HA-SH microhydrogel.
Figure 4:
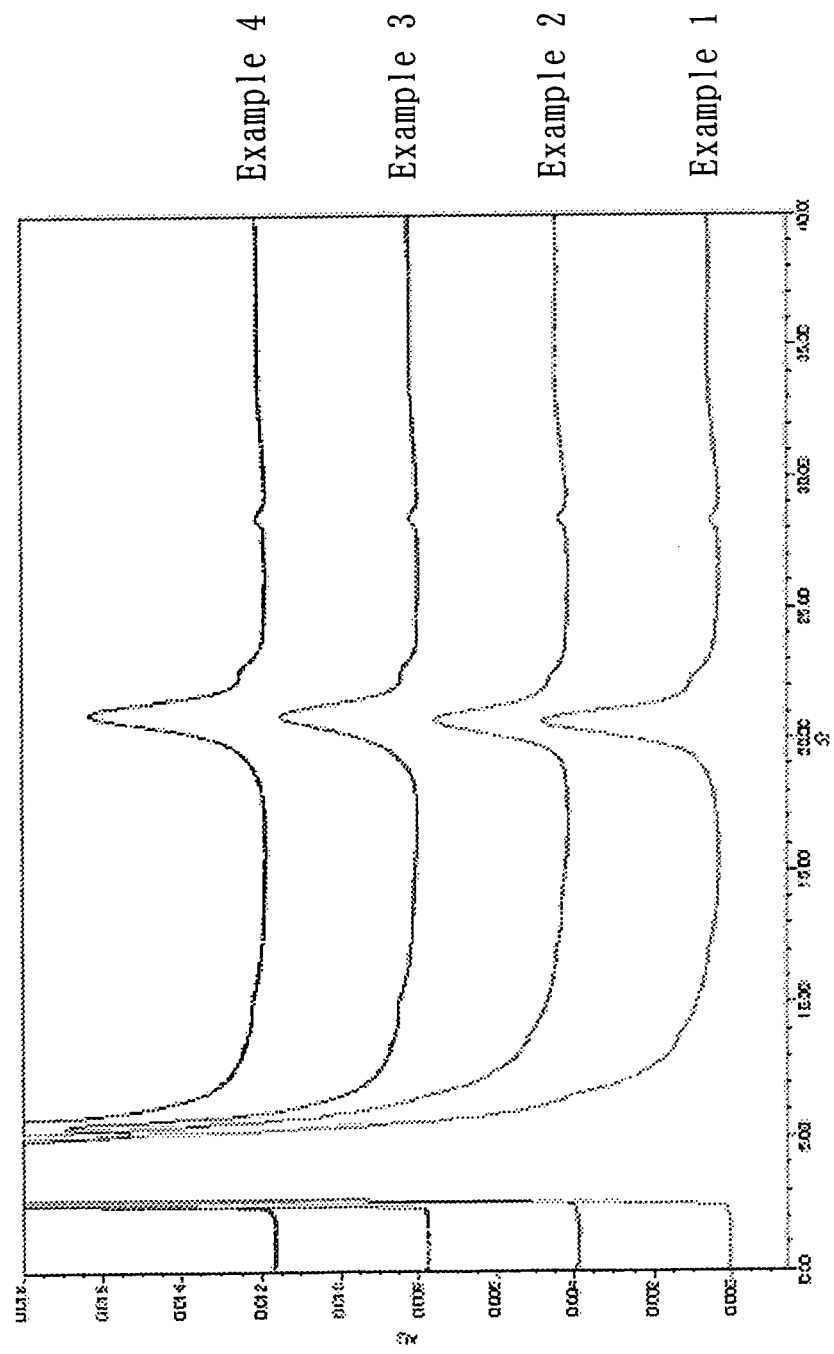
FIG. 4 A graph showing one example of the RP-HPLC results, which shows the amount of EPO recovered from the crosslinked HA-SH microhydrogel microparticles obtained in Examples 1 to 4. Starting from the bottom, the curves correspond to the microparticles obtained in Examples 1, 2, 3 and 4, respectively.

Thermogravimetry analysis (TGA) was carried out to determine the water content of the microparticles prepared in Example 3 (FIG. 3). The water content was about 15%.

Test Example 2

Measurement of EPO Recovery Rate in EPO-Encapsulated Crosslinked Hyaluronic Acid Microparticles The microparticles prepared in Examples 1 to 8 and Comparative Example 2 (5 mg each) were each dispersed in 0.5 mL PBS, supplemented with 0.25 units of Hyaluronidase SD (HAse; Seikagaku Corporation, Japan) and enzymatically treated at 25° C. for 3 hours to completely digest the microparticles. Likewise, the gel prepared in Comparative Example 1 (0.25 mL) was supplemented with 0.75 mL PBS (pH 7.4) containing 0.5 units of Hyaluronidase SD (Seikagaku Corporation, Japan) and enzymatically treated at 25° C. for 1 day to completely digest the gel. The resulting solutions after enzymatic treatment (0.15 mL each) were used as sample solutions. These sample solutions were measured by reversed-phase chromatography (RP-HPLC) using a 0.1 mg/mL aqueous EPO solution as a standard solution to calculate the EPO concentration in each sample solution from the peak area ratio between standard solution and sample solution. The recovery rate was calculated as the amount of EPO determined by RP-HPLC relative to the amount of EPO added (0.1 mg/gel).

High performance liquid chromatography analysis on a reversed-phase column (RP-HPLC) was carried out using a Waters 600S controller, a 717 plus autosampler and a 486 infrared absorption spectrometer (Waters) under the following measurement conditions.

Column: C4 (particle diameter: 5 μm, size: 4.6×250 mm)
Mobile phases:
A: water/acetonitrile/trifluoroacetic acid=400/100/1
B: water/acetonitrile/trifluoroacetic acid=100/400/1
Flow rate: 1 mL/minute, eluted with a gradient of the mobile phases A/B=65/35 to 0/100
Column temperature: around room temperature
Sample temperature: 4° C.
Detection wavelength: UV 280 nm
Analysis software: Millenium 32 ver. 3.21

When measured as described above, the recovery rate of EPO relative to the initial amount was as follows.
Examples 1 to 4: 90% to 95%
Examples 5 and 6: 80% to 85%
Examples 7 and 8: 75% to 80%
Comparative Examples 1 and 2: 90% to 95%

These results confirmed that the recovery rate was improved by addition of STT and/or a surfactant.

Test Example 3

Sustained Release of EPO from the Prepared EPO-Encapsulated HA Hydrogels

The microhydrogel prepared in Example 3 (20 mg) and the bulk gel prepared in Comparative Example 1 (250 μL) were each incubated in 2 mL PBS at 37° C. and sampled over time in 200 μL aliquots. The amount of EPO released into the buffer was determined by RP-HPLC.

Figure 5:
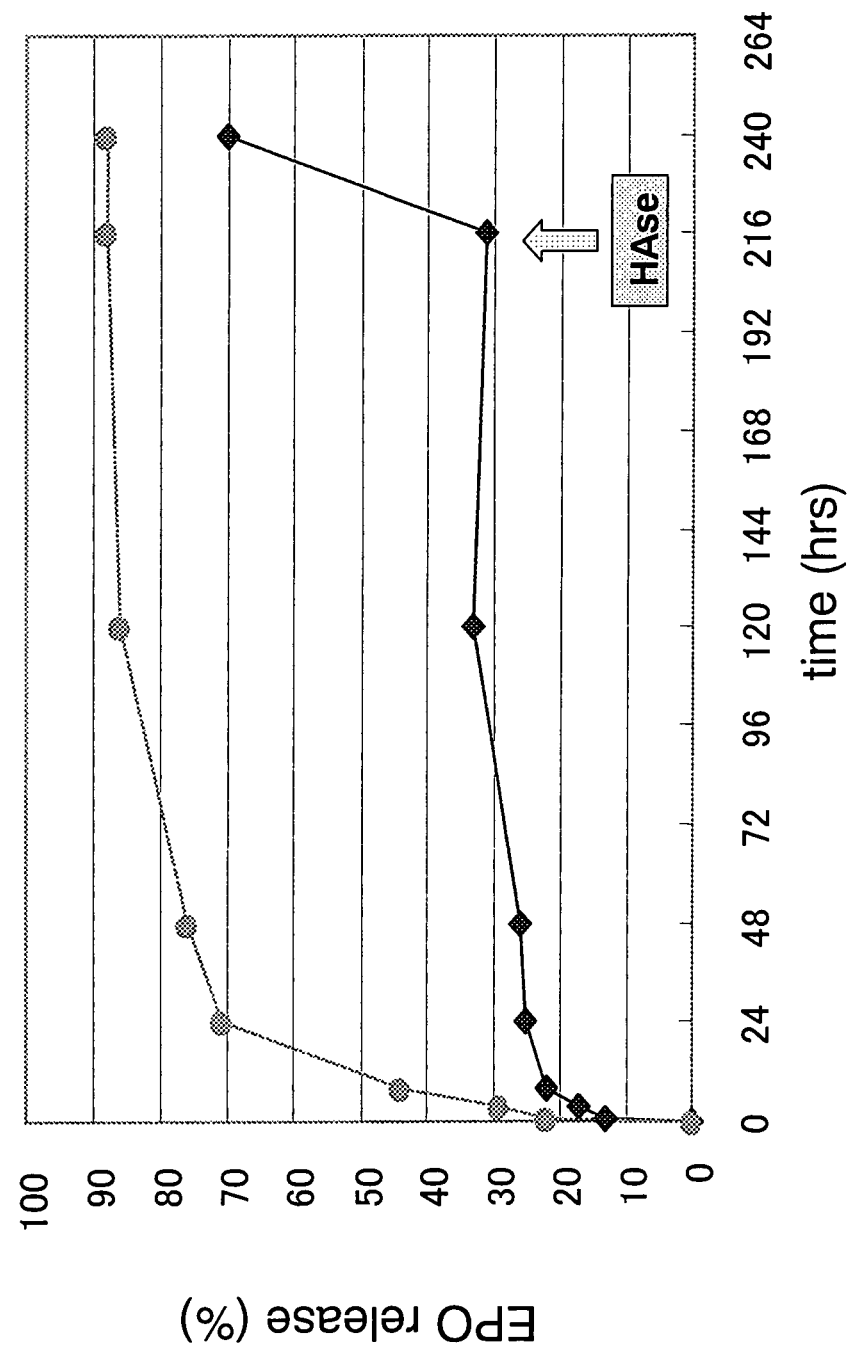
FIG. 5 A graph showing the release profile of EPO from the HA gels obtained in Example 3 and Comparative Example 1.
Figure 6:
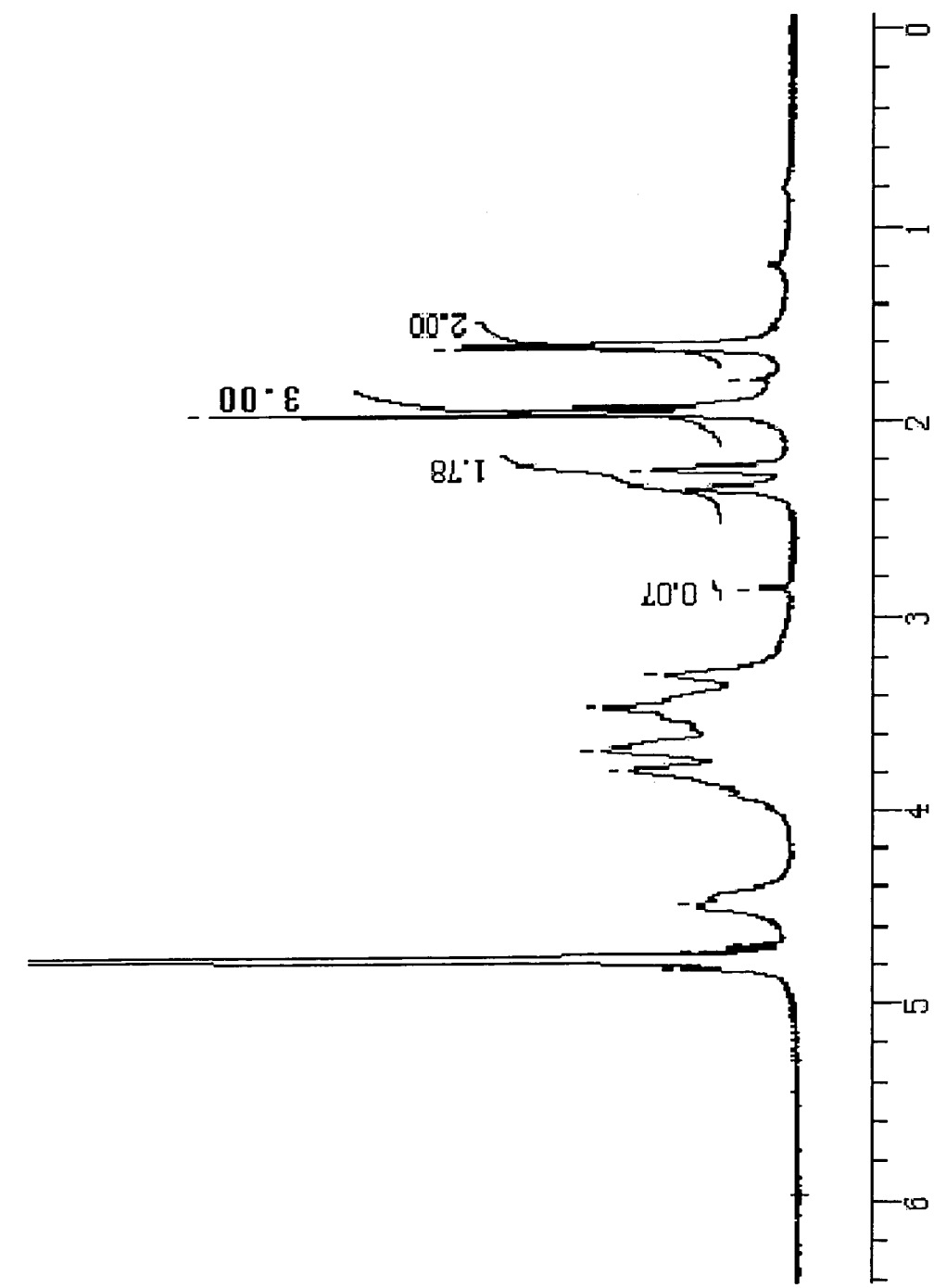
FIG. 6 One example of the $^1$H-NMR results measured for the hyaluronic acid derivative (HA-HZ) obtained in Example 9-1.
Figure 7:
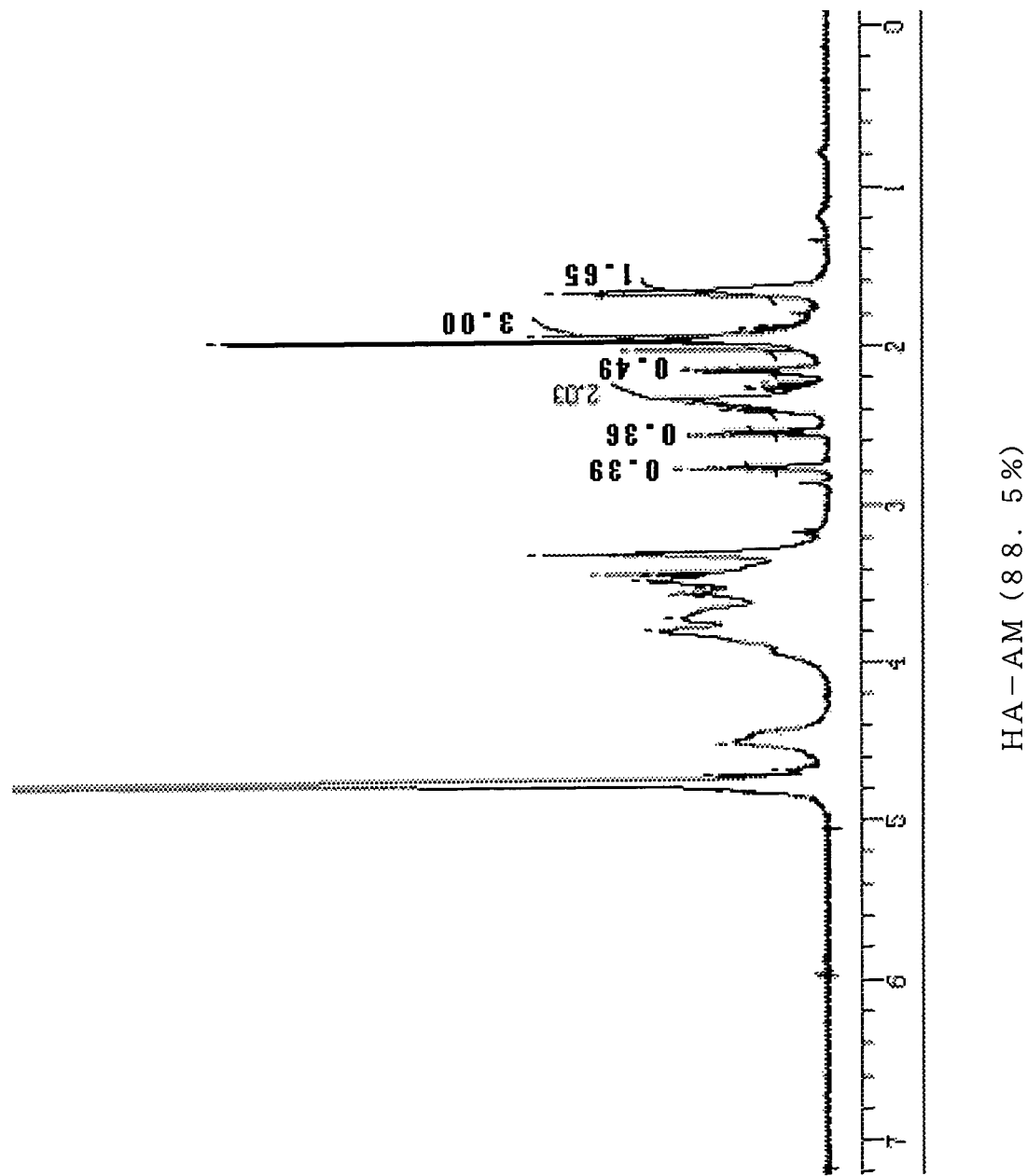
FIG. 7 One example of the $^1$H-NMR results measured for the hyaluronic acid derivative (HA-HZ-SH) obtained in Example 9-2.
Figure 8:
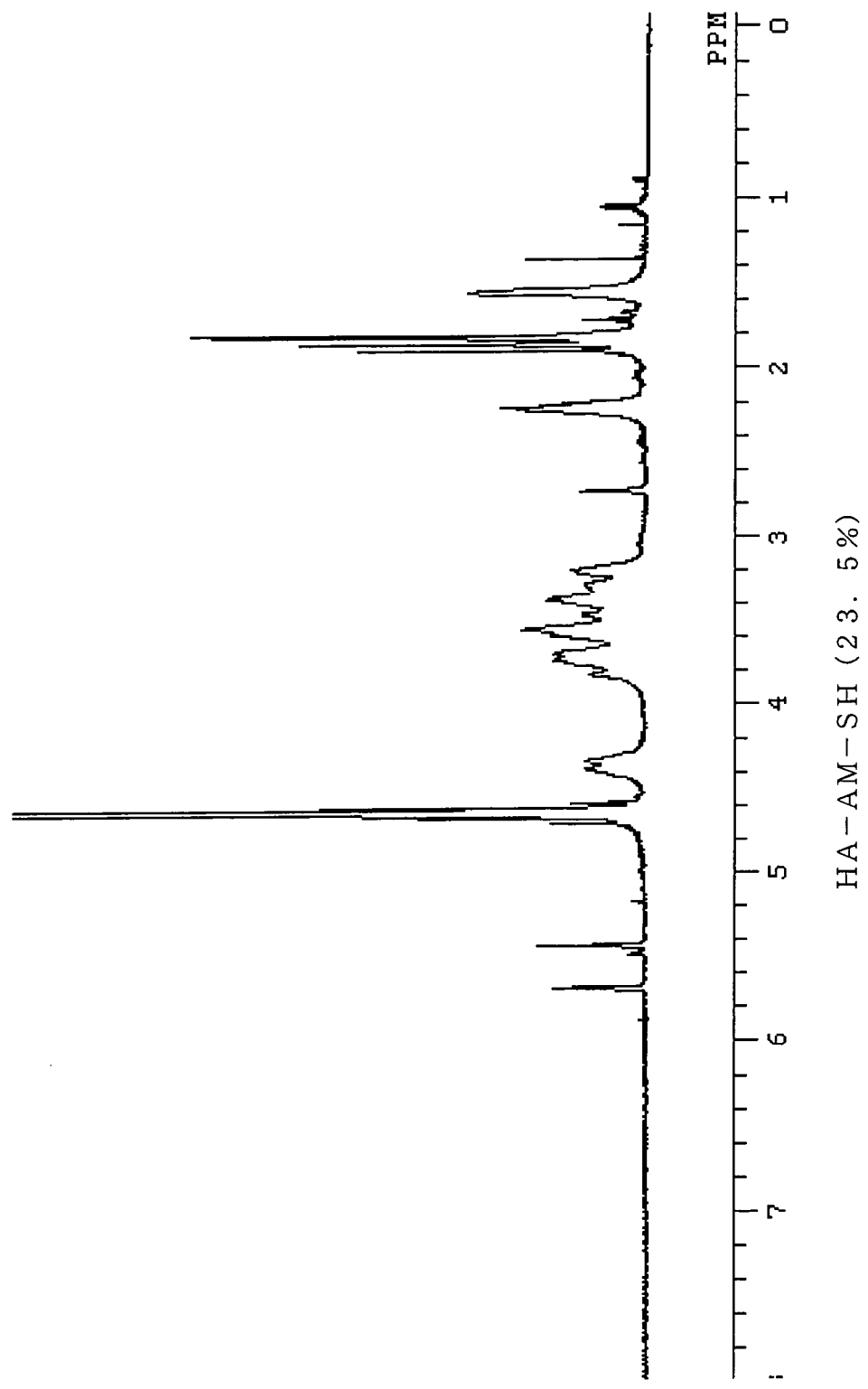
FIG. 8 One example of the $^1$H-NMR results measured for the hyaluronic acid derivative (HA-HZ-MA) obtained in Example 10.
Figure 9:
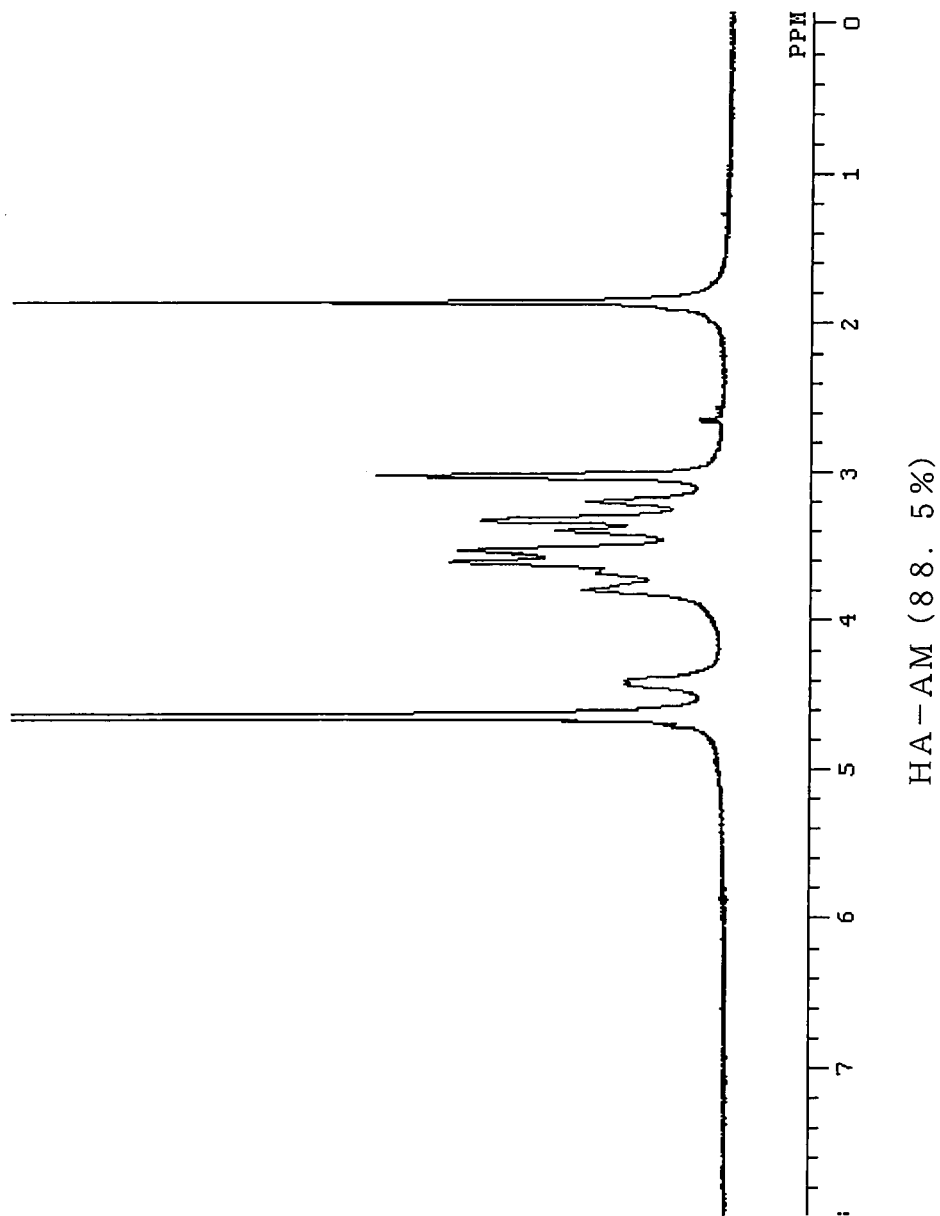
FIG. 9 One example of the $^1$H-NMR results measured for the hyaluronic acid derivative (HA-AM) obtained in Example 11-1.
Figure 10:
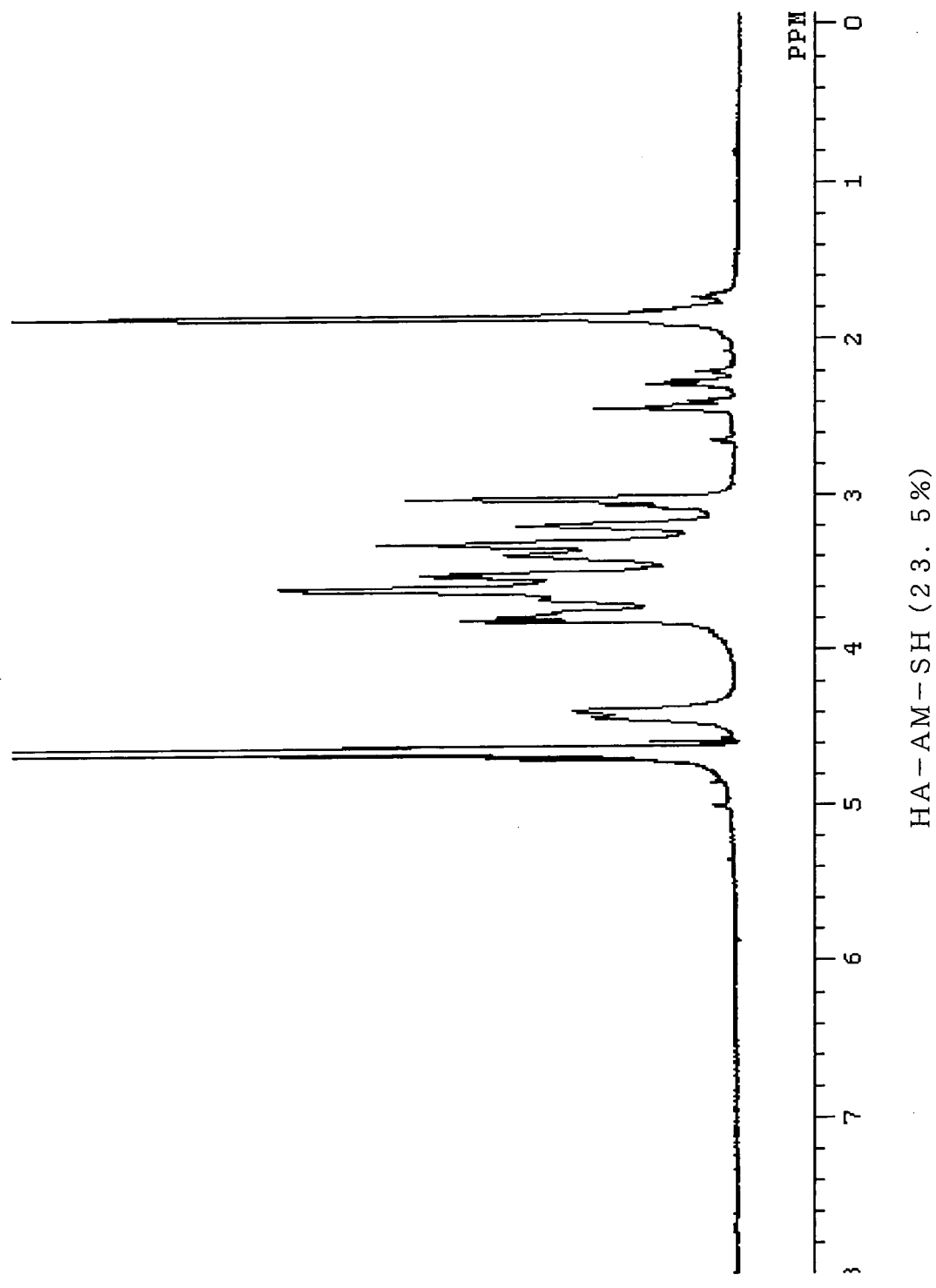
FIG. 10 One example of the ¹H-NMR results measured for the hyaluronic acid derivative (HA-AM-SH) obtained in Example 11-2.
Figure 11:
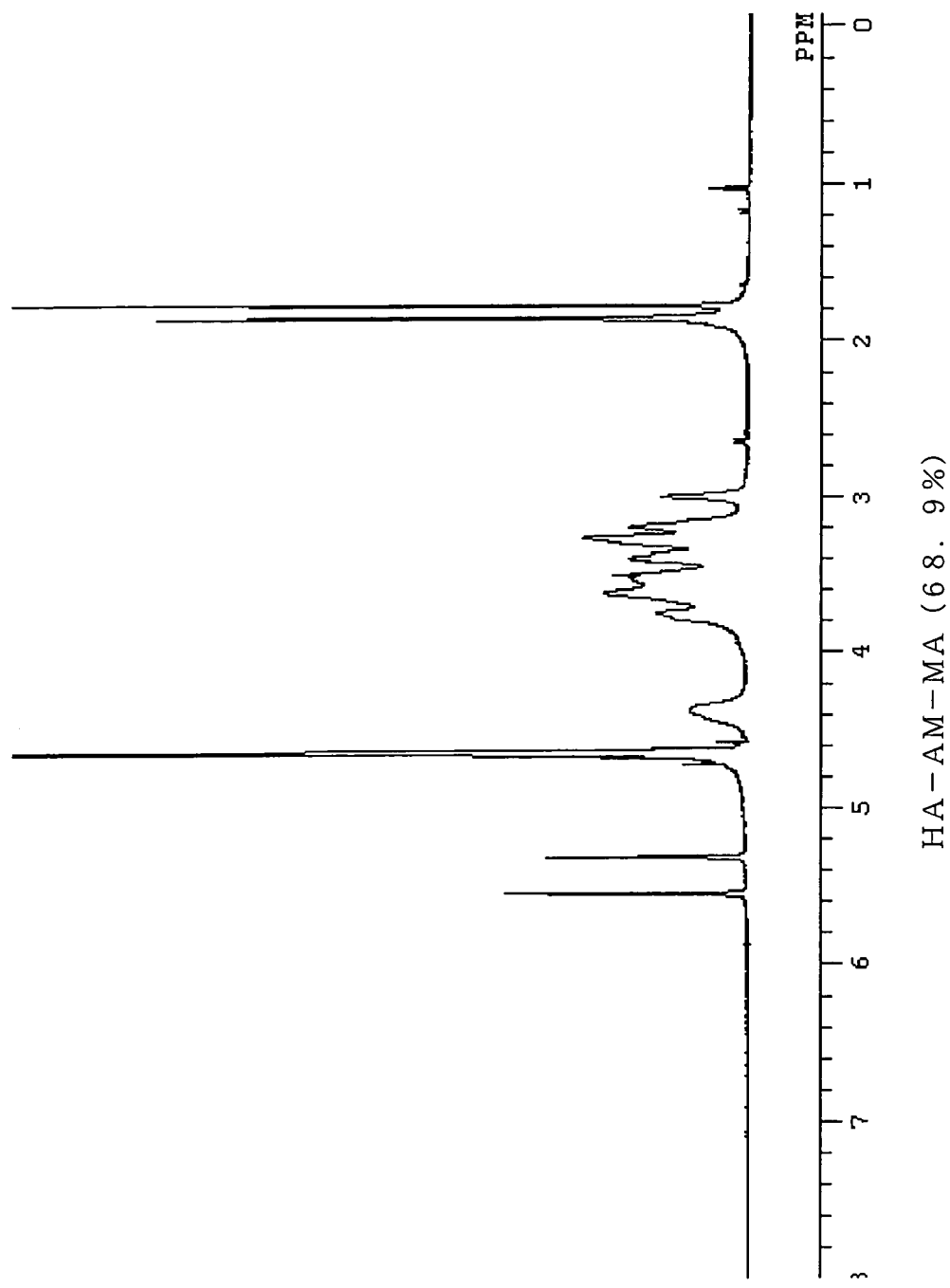
FIG. 11 One example of the ¹H-NMR results measured for the hyaluronic acid derivative (HA-AM-MA) obtained in Example 11-1.

FIG. 5 shows the release profile of EPO from each gel, as determined by assuming that the EPO collected from the gel digested which hyaluronidase immediately after gel preparation is set to 100%. After 9 days, hyaluronidase (HAse) was added.

The results indicate that EPO in the gels remains undenatured and is rapidly released from the gel obtained in Comparative Example 1 because of its low crosslinking density. The results also indicate that the microgel of Example 3 allows sustained release of about 30% EPO over about 5 days because of its high crosslinking density, while 40% of EPO is not released by diffusion but can be released upon enzymatic digestion.

By using drug-carrying microparticles, in which a drug is encapsulated in crosslinked hyaluronic acid, as illustrated in the above examples, it is possible to prepare injectable sustained-release formulations which allow long-term release of drugs such as proteins or peptides crosslinked in situ, dried and encapsulated in gel microparticles while retaining their biological activity.

Example 9

Example 9-1

Synthesis of Hydrazide (HZ) Group-Modified Hyaluronic Acid Derivative HA-HZ (Mixed Solvent Technique)

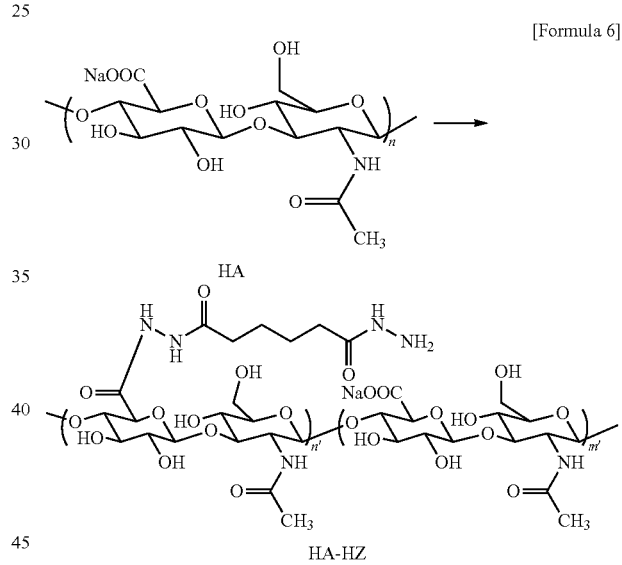

[Formula 6]

HA having a molecular weight of $2 \times 10^5$ daltons (76.0 mg, Denki Kagaku Kogyo Kabushiki Kaisha, Japan) was dissolved at a concentration of 0.1% in distilled water/EtOH=50/50 and adjusted with 5N hydrochloric acid to pH 4.7 to 4.8. 1-Ethyl-3-(3-dimethylaminopropyl)-carbodiimide (EDC) and adipic acid dihydrazide (ADH) were added at a molar ratio of HA unit (1 unit=repeated unit of N-acetylglucosamine-glucuronic acid):EDC:ADH=1:4:40, and reacted at room temperature for 2 hours while adjusting the mixture with 5N hydrochloric acid to maintain a pH of 4.7 to 4.8. The reaction mixture was dialyzed sequentially against large excess volumes of a 100 mM sodium chloride solution, a 25% ethanol solution and distilled water (SpectraPor 7, molecular weight cutoff (MWCO): 12 k-14 k daltons) and lyophilized to give 57.0 mg of the titled hydrazide (HZ) group-modified hyaluronic acid (HA-HZ). The introduction rate of HZ groups in the resulting HA-HZ was determined as the introduction rate of ADH by proton NMR (calculated by comparing N-acetyl groups (1.85 ppm) for HA and ADH-derived 4 methylene groups (1.5, 2.1 and 2.25 ppm) for HZ). The introduction rate of HZ was 47%.

Example 9-2

Synthesis of Mercapto (SH) Group-Modified Hyaluronic Acid Derivative HA-HZ-SH

HA-HZ ⟶

[Formula 7]

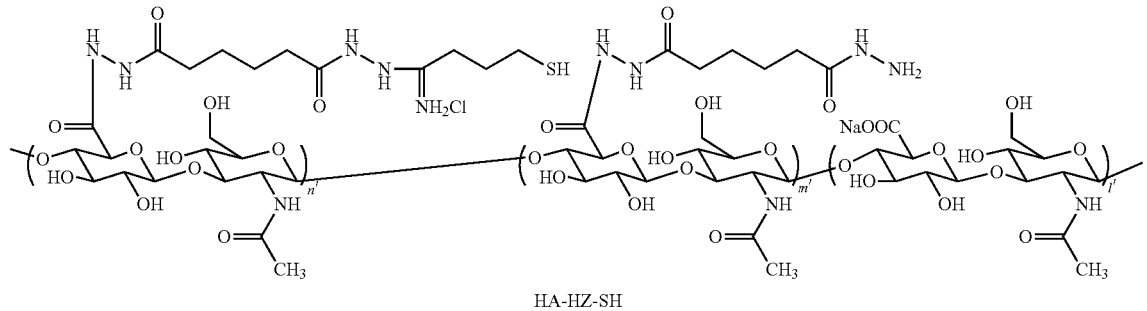

HA-HZ-SH

HA-HZ synthesized in the same manner as used in Example 9-1 (100 mg) was dissolved in 5 mL of 100 mM phosphate buffer, pH 8 (HA-HZ: 2% w/v), followed by addition of iminothiolane (ITL) (at a molar ratio of HZ/ITL=1/2). The mixture was reacted while stirring at room temperature for 2 hours and then precipitated in ethanol, washed three times and dried. The introduction rate of SH groups in the resulting HA-HZ-SH was determined by proton NMR, indicating that the introduction rate of SH was 37.5 mol % (calculated by comparing N-acetyl groups in HA and HA-HZ-SH (1.9 ppm, 3H) and methylene groups in the ITL-derived moiety of HA-HZ-SH (2.1 ppm and 2.7 ppm, 2H each)).

Example 10

Synthesis of Methacryloyl (MA) Group-Modified Hyaluronic Acid Derivative HA-HZ-MA The same procedure as used in Batch 3 of Example 1-1 was repeated to synthesize HA-HZ (63% of carboxylic acid in HA was modified with HZ), except that the molecular weight of HA was set to $2 \times 10^4$ daltons. The resulting HA-HZ was dissolved in distilled water, followed by addition of 1M phosphate buffer (pH 8.8) to prepare 0.1 M phosphate buffer having a HA concentration of 50 mg/mL. Methacrylic anhydride was added dropwise in an amount of 20-fold equivalents relative to HZ and reacted while stirring overnight at room temperature. After precipitation in tetrahydrofuran, the precipitate was collected and dried. This precipitate was dissolved in distilled water, precipitated again in tetrahydrofuran and then dried. The dried product was then dissolved in distilled water and lyophilized to give the titled HA-HZ-MA.

The introduction rate of methacryloyl groups was determined by proton NMR (calculated by comparing methyl protons in N-acetyl groups (1.8 to 1.9 ppm) for HA and $CH_2=$ in methacryloyl groups (5.5 to 6.1 ppm) for MA). The introduction rate of MA was 22%.

[Formula 8]

HA-HZ ⟶

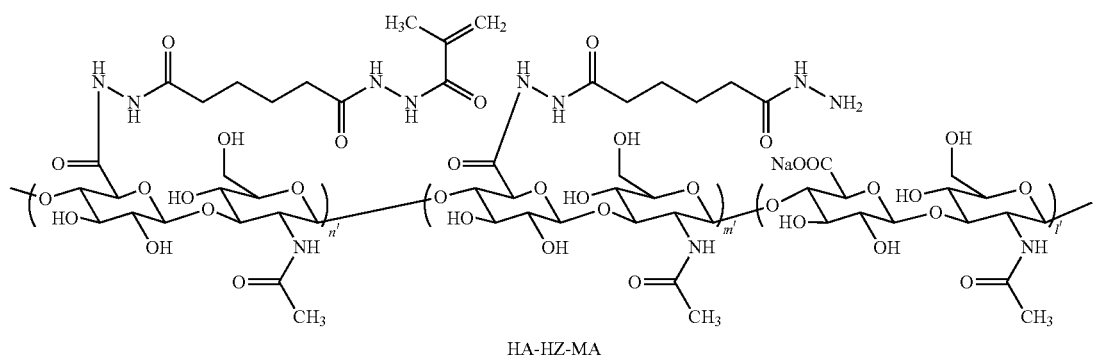

HA-HZ-MA

Example 11

Example 11-1

Synthesis of Amino (AM) Group-Modified Hyaluronic Acid Derivative HA-AM

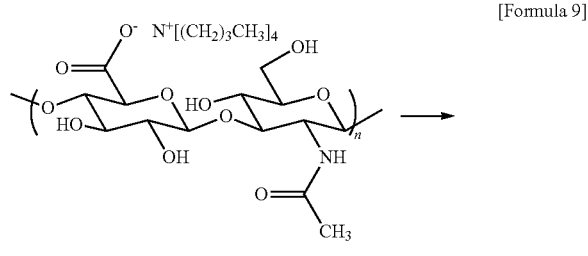

[Formula 9]

HA-TBA

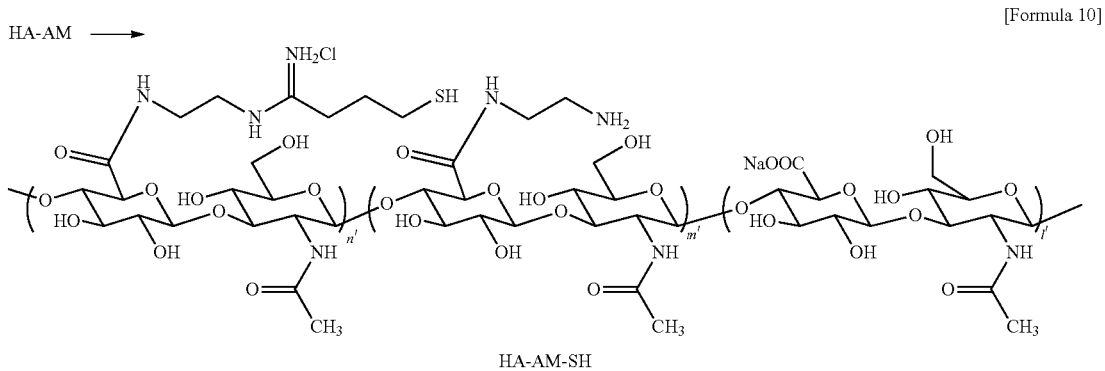

[Formula 10]

HA-AM-SH

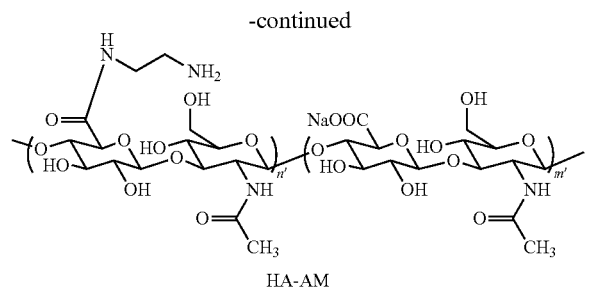

HA-AM

Sodium hyaluronate (HA) having a molecular weight of $2.0 \times 10^5$ daltons (Denki Kagaku Kogyo Kabushiki Kaisha, Japan) was converted into a tetrabutylammonium (TBA) salt form using DOWEX 50WX8-400 (Sigma-Aldrich Corporation) which had been treated with tetrabutylammonium hydroxide (Sigma-Aldrich Corporation).

After the resulting tetrabutylammonium salt of hyaluronate (HA-TBA) was dissolved at a concentration of 2.0 mg/mL in DMSO (Wako Pure Chemical Industries, Ltd., Japan), ethylenediamine (EDA; Sigma-Aldrich Corporation) and BOP (Wako Pure Chemical Industries, Ltd., Japan) were added in this order at an equivalent ratio of HA unit/BOP/EDA=1/2.5/50 (mol/mol/mol) and reacted overnight at room temperature. After 1M aqueous sodium chloride was added in an amount of half the volume of the reaction solution, the resulting mixture was reduced to pH 3 with 5N HCl and further neutralized with 2N NaOH. The reaction mixture was dialyzed sequentially against large excess volumes of 0.3 M aqueous sodium chloride and distilled water (SpectraPor 4, molecular weight cutoff (MWCO): 12 k-14 k daltons); ultrafiltered and lyophilized to give the titled amino group-modified hyaluronic acid (HA-AM).

The introduction rate of amino groups was determined by proton NMR (calculated by comparing methyl protons in N-acetyl groups (1.8 to 1.9 ppm) for HA and methylene protons in the ethylenediamine moiety (2.9 to 3.1 ppm) for AM). The introduction rate was 88.5%.

Example 11-2

Synthesis of Mercapto (SH) Group-Modified Hyaluronic Acid Derivative HA-AM-SH

After HA-AM obtained above was dissolved at 2 mg/mL in carbonate buffer (pH 9), iminothiolane (Pierce) was added in an amount of 0.5- or 1-fold equivalent relative to HA units and reacted for 45 minutes at room temperature. After the reaction, the reaction mixture was purified on a PD-10 column (Amersham Biosciences) equilibrated with 0.005 N aqueous HCl, and then lyophilized to remove the solvent. The resulting polymer was washed with an excess volume of ethanol and dried under reduced pressure to give HA-AM-SH.

The introduction rate of mercapto groups was determined by proton NMR in a state containing a reducing agent tris(2-carboxyethylphosphine)hydrochloride (TCEP) (calculated by comparing methyl protons in N-acetyl groups (1.8 to 1.9 ppm) for HA and methylene protons adjacent to mercapto groups (2.4 to 2.7 ppm) for SH). The introduction rate was 16.5% and 23.5% in the respective cases.

Example 11-3

Synthesis of Methacryloyl (MA) Group-Modified Hyaluronic Acid Derivative HA-AM-MA

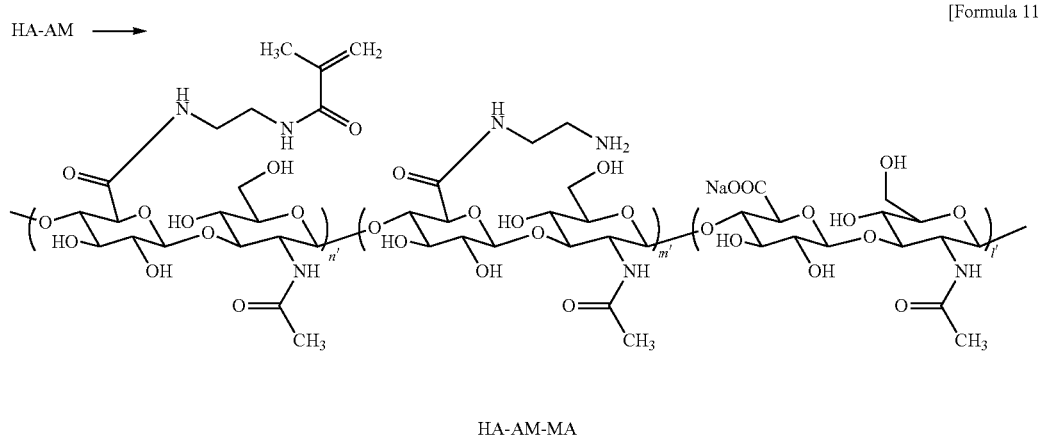

[Formula 11]

After HA-AM obtained above was dissolved at 10 mg/mL in phosphate buffer (pH 7), methacrylic acid activated with 1-ethyl-3-(3-dimethylaminopropyl)carbodiimide (EDC) was added in an amount of 0.5-, 1.0- or 2.0-fold equivalents relative to HA units and reacted for 2 hours at room temperature. After the reaction, the reaction mixture was dialyzed sequentially against 0.3 M aqueous sodium chloride and distilled water (SpectraPor 4, molecular weight cutoff (MWCO): 12 k-14 k daltons) for purification purposes, and then lyophilized to give the above polymer.

The introduction rate of methacryloyl groups was determined by proton NMR (calculated by comparing methyl protons in N-acetyl groups (1.8 to 1.9 ppm) for HA and $CH_2=$ in methacryloyl groups (5.5 to 6.1 ppm) for MA). The introduction rate was 14.8%, 31.9% and 68.9% in the respective cases.

Example 12

Effect of Thermal Treatment on Microparticles (Swelling Inhibition)

HA-HZ-SH (introduction rate of SH groups: 37.5 mol %) synthesized in Example 9-2 (100 mg) was dissolved in 8.5 mL of distilled water. To this solution, 1 mL of 100 mM phosphate buffer (PB; pH 7) was added and 5 mg of Tween-80 was further dissolved, followed by addition of STT (2.3 mg, 1/10-fold molar amount relative to SH groups). This solution was spray-dried under the same conditions as used in Example 1-3 (Solution feed rate 0.5 mL/min, Aspiration speed=100%) to obtain microparticles. These microparticles were cured in a 50° C. thermostat (DN-42, Yamato Scientific Co., Ltd., Japan) and sampled after 24 and 72 hours.

Test Example 4

Figure 12:
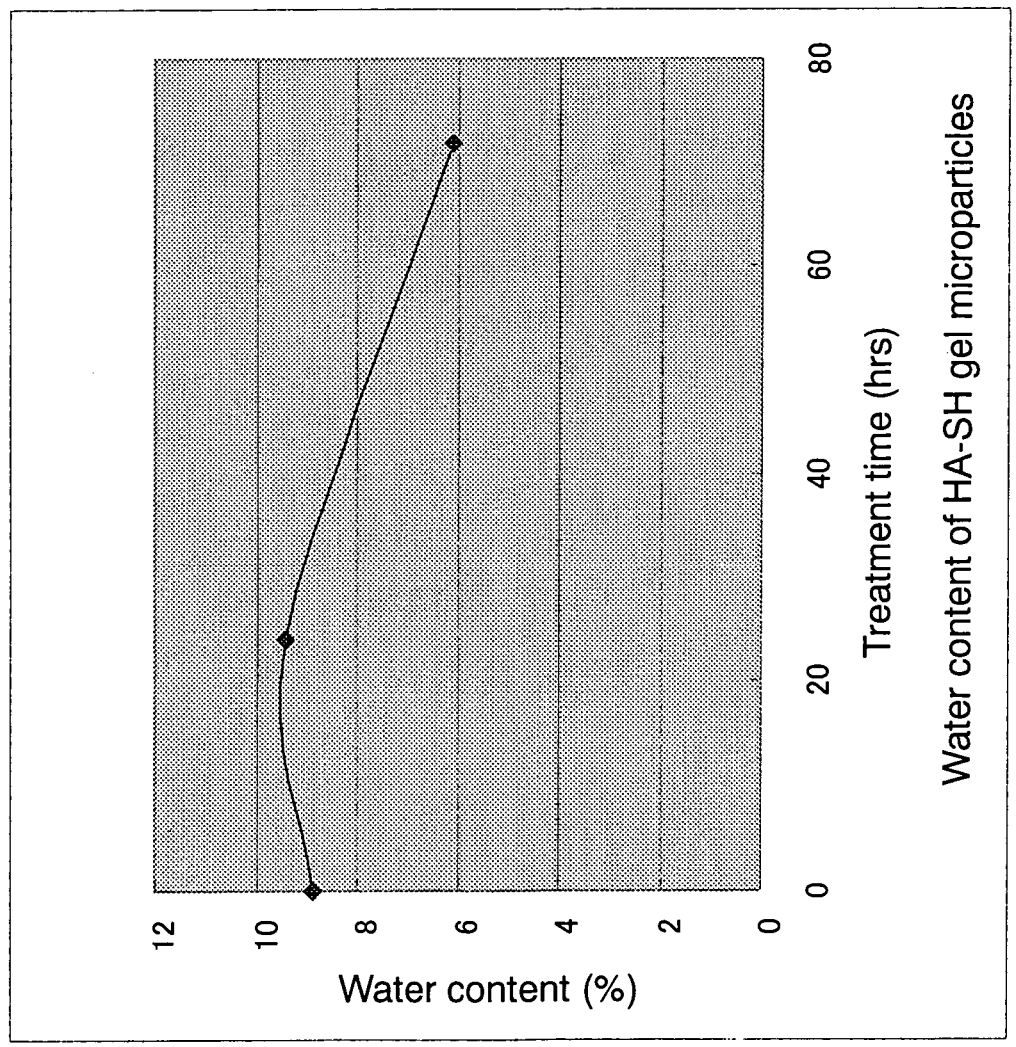
FIG. 12 A graph showing curing-induced changes in the water content of the particles obtained in Example 12.
Figure 13:
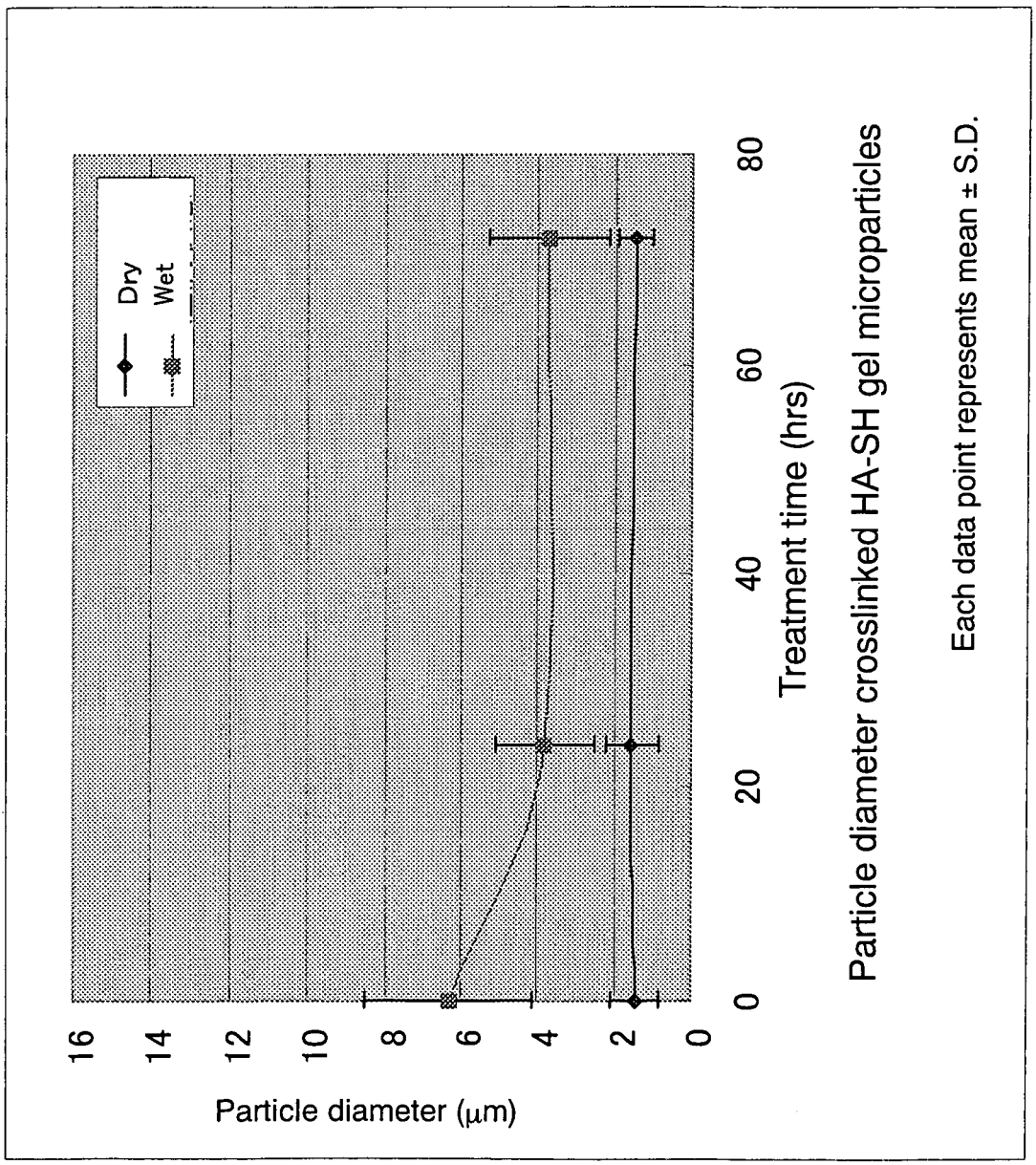
FIG. 13 A graph showing a curing-induced inhibitory effect on swelling of the particles obtained in Example 12.

Each sample sampled in Example 12 was measured for particle water content by TGA. The results obtained are shown in FIG. 12. Likewise, 30 particles were randomly selected from each sample and measured for their Feret's diameter (dry particle diameter) by microscopic image analysis. Further, the sampled particles were swollen by addition of PBS containing Tween-80 (0.05%) and measured for their wet particle diameter in the same manner. The results obtained are shown in FIG. 13. These results confirmed that the degree of swelling was reduced when the particles were incubated for 24 hours. This would be because incubation at 50° C. for 24 hours may increase crosslinking within the particles.

Example 13

Preparation of Crosslinked HA-HZ-MA Microgels

HA-HZ-MA synthesized in Example 10 (100 mg) was dissolved in 6 mL of distilled water. To this solution, 1 mL of 100 mM phosphate buffer (PB; pH 8.5) containing DTT (11 mg) and TEA (32.5 µL) was added and further mixed with distilled water (3 mL). This solution was spray-dried under the same conditions as used in Example 12 (exhaust temperature 65° C.) to obtain microparticles. These microparticles were cured in a 50° C. thermostat (DN-42, Yamato Scientific Co., Ltd., Japan) for about 72 hours to obtain particles.

Test Example 5

The particles obtained in Example 13 were placed on a slide and, after addition of PBS (pH 7), were then observed for their state under a microscope, indicating that the particles were not dissolved in PBS. This microscopic observation confirmed crosslinkage formation caused by addition reaction between a mercapto group and an unsaturated bond in the microparticles obtained in Example 13.

INDUSTRIAL APPLICABILITY

The sustained-release drug carrier of the present invention allows in situ chemical crosslinking of drugs such as proteins or peptides and their encapsulation into HA gels while retaining their biological activity, and enables the provision of injectable microparticles which allow long-term sustained release of the drugs such as proteins or peptides at high recovery rates.

The invention claimed is:

1. A method for preparing crosslinked polysaccharide microparticles having an average particle diameter of 0.01 µm to 150 µm, which method comprises the following steps:

a) preparing a dilute solution containing (1) a polysaccharide derivative having at least one crosslinkable functional group in a range of 0.1 to 5% (w/v) and (2) a crosslinking agent;
b) dispersing the solution by spraying to form microparticulate droplets; and
c) concentrating the solution contained in the droplets to facilitate a crosslinking addition reaction of the polysaccharide derivative between a mercapto group and an unsaturated C—C bond, thereby providing microparticles having an average particle diameter of 0.01 μm to 150 μm;
wherein steps b) and c) are carried out in a spray drying procedure;
wherein the polysaccharide derivative is a hyaluronic acid derivative comprising at least one repeating unit represented by Formula (I);

$$\text{(I)}$$

wherein $X_2$ represents —$Y_1$-$Q_1$-$Y_2$—N(—$R_2$)—$Y_3$-$Q_2$-SH, —NHCO—$(CH_2)_4$—CONH—NH—C(=NH)—$(CH_2)_3$—SH, —$(CH_2)_2$—NH—C(=NH)—$(CH_2)_3$—SH, or —$(CH_2)_2$—O—$(CH_2)_2$—O—$(CH_2)_2$—NH—C(=NH)—$(CH_2)_3$—SH,
$R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group,
$R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{2-6}$ alkenyl group, a linear or branched $C_{2-6}$ alkynyl group, a linear or branched $C_{1-16}$ alkylcarbonyl group, a linear or branched $C_{2-6}$ alkenylcarbonyl group, a linear or branched $C_{2-6}$ alkynylcarbonyl group or —$SO_2OH$,
$Y_1$ represents a single bond, —N(—$R_3$)CO—, —N(—$R_3$)—, —CO— or —$CH_2CO$—,
$Y_2$ represents a single bond, —CON(—$R_4$)— or —N(—$R_4$)—,
$Q_1$ represents a linear or branched $C_{1-10}$ alkylene group, a linear or branched $C_{1-10}$ hydroxyalkylene group, a polyalkylene oxide group, a polypeptide group or a polyester group,
$R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group,
$Y_3$ represents a single bond, —CO—, —$CO_2$—, —$CH_2$—CH(OH)— or —CONH—, and
$Q_2$ represents a linear or branched $C_{1-10}$ alkylene group, a linear or branched $C_{1-10}$ hydroxyalkylene group, a polyalkylene oxide group, a polypeptide group or a polyester group, and the crosslinking agent is a compound having two or more unsaturated C—C bond-containing groups; or
the polysaccharide derivative is a hyaluronic acid derivative comprising at least one repeating unit represented by Formula (II):

$$\text{(II)}$$

wherein $X_3$ represents —$Y_1$-$Q_1$-$Y_2$—N(—$R_2$)—$Y_3$-$Q_4$ or —N(—$R_2$)—$Y_3$-$Q_4$,
$R_1$ represents a hydrogen atom, a linear or branched $C_{1-10}$ alkyl group, a linear or branched $C_{1-10}$ hydroxyalkyl group, a polyalkylene oxide group, a polypeptide group or a polyester group,
$R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{2-6}$ alkenyl group, a linear or branched $C_{2-6}$ alkynyl group, a linear or branched $C_{1-6}$ alkyl carbonyl group, a linear or branched $C_{2-6}$ alkenylcarbonyl group, a linear or branched $C_{2-6}$ alkynylcarbonyl group or —$SO_2OH$,
$Y_1$ represents a single bond, —N(—$R_3$)CO—, —N(—$R_3$)—, —CO— or —$CH_2CO$—,
$Y_2$ represents a single bond, —CON(—$R_4$)— or —N(—$R_4$)—,
$Y_3$ represents a single bond, —CO— or —$CH_2CO$—,
$Q_1$ represents a linear or branched $C_{1-10}$ alkylene group, a linear or branched $C_{1-10}$ hydroxyalkylene group, a polyalkylene oxide group, a polypeptide group or a polyester group,
$R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group or a polyester group,
$Q_4$ represents a linear or branched $C_{2-10}$ alkenyl group, or a linear or branched $C_{2-10}$ alkynyl group, and the crosslinking agent is a compound having two or more mercapto groups; and
wherein the method is performed so as to crosslink the hyaruronic acid derivative during concentration and drying.

2. The method according to claim 1, wherein the resulting microparticle is a drug carrier.

3. The method according to claim 2, wherein the crosslinked polysaccharide microparticles are injectable.

4. The method according to claim 2, wherein the drug is a protein.

5. The method according to claim 1, wherein the resulting microparticle is a sustained-release drug carrier.

6. The method according to claim 5, wherein the dilute solution before the crosslinking reaction contains a drug, and the drug is held in the microparticles obtained after the crosslinking reaction.

7. The method according to claim 6, wherein the crosslinking reaction does not cause drug denaturation in the presence of the drug.

8. The method according to claim 5, wherein the sustained release period of the carrier is 24 hours or more.

9. The method according to claim 5, wherein the sustained release period of the carrier is 5 days or more.

10. The method according to claim 5, wherein the drug is released upon enzymatic digestion.

11. The method according to claim 1, wherein the dilute solution before the crosslinking reaction contains a drug, and the drug is held in the microparticles obtained after the crosslinking reaction.

12. The method according to claim 11, wherein the crosslinking reaction does not cause drug denaturation in the presence of the drug.

13. The microparticle according to claim 1, wherein the crosslinkable functional group is a mercapto group, and the crosslinking reaction is a reaction in which crosslinkages are formed by disulfide formation.

\* \* \* \* \*